United States Patent
Belliard et al.

(10) Patent No.: US 12,232,777 B2
(45) Date of Patent: Feb. 25, 2025

(54) DYNAMIC SUPPORT SYSTEM

(71) Applicant: Zimmer Spine S.A.S., Bordeaux (FR)

(72) Inventors: Karl P Belliard, La Membrolle (FR); Bruno Ichelmann, Limoges (FR); Wouter ten Tusscher, Ludon Medoc (FR)

(73) Assignee: LDR Medical, S.A.S. (FR)

( * ) Notice: Subject to any disclaimer, the term of this patent is extended or adjusted under 35 U.S.C. 154(b) by 130 days.

(21) Appl. No.: 16/923,789

(22) Filed: Jul. 8, 2020

(65) Prior Publication Data

US 2020/0337733 A1    Oct. 29, 2020

Related U.S. Application Data

(63) Continuation of application No. 16/135,754, filed on Sep. 19, 2018, now abandoned, which is a continuation of application No. 15/172,631, filed on Jun. 3, 2016, now Pat. No. 10,098,670.

(30) Foreign Application Priority Data

Jun. 4, 2015    (EP) .................................... 15290148

(51) Int. Cl.
A61B 17/70    (2006.01)

(52) U.S. Cl.
CPC ........ *A61B 17/704* (2013.01); *A61B 17/7002* (2013.01); *A61B 17/7008* (2013.01); *A61B 17/7032* (2013.01); *A61B 17/7037* (2013.01); *A61B 17/7053* (2013.01); *A61B 17/7005* (2013.01); *A61B 17/7022* (2013.01)

(58) Field of Classification Search
CPC ............................................... Y10T 403/7188
See application file for complete search history.

(56) References Cited

U.S. PATENT DOCUMENTS

| | | | |
|---|---|---|---|
| 6,436,099 B1 * | 8/2002 | Drewry | A61B 17/7022 606/303 |
| 8,057,516 B2 | 11/2011 | Zylber et al. | |
| 8,366,745 B2 | 2/2013 | Jackson | |

(Continued)

FOREIGN PATENT DOCUMENTS

| | | |
|---|---|---|
| EP | 1800614 A1 | 6/2007 |
| EP | 2174608 A1 | 4/2010 |

(Continued)

OTHER PUBLICATIONS

"U.S. Appl. No. 15/172,631, Non Final Office Action mailed Sep. 20, 2017", 10 pgs.

(Continued)

*Primary Examiner* — Tessa M Matthews
(74) *Attorney, Agent, or Firm* — Sheridan Ross P.C.

(57) ABSTRACT

A spinal stabilization system including an insert positionable in the channel of the housing of a vertebral anchor, and an associated support construct including a spacer and at least one cord extending through the insert. In some instances the construct includes first and second cords extending through first and second bores of the insert. A clamping member clamps the cord(s) in the insert. In some instances the clamping member includes first and second tabs movable in channels in first and second flanges of the insert.

20 Claims, 32 Drawing Sheets

(56) References Cited

U.S. PATENT DOCUMENTS

| | | | |
|---|---|---|---|
| 8,377,099 B1 | 2/2013 | Stauber | |
| 8,740,945 B2 | 6/2014 | Hestad et al. | |
| 8,795,336 B2 | 8/2014 | Biedermann et al. | |
| 8,870,926 B2 | 10/2014 | Kumar et al. | |
| 9,044,274 B2* | 6/2015 | Gunn | A61B 17/7032 |
| 9,393,047 B2 | 7/2016 | Jackson et al. | |
| 10,098,670 B2 | 10/2018 | Belliard et al. | |
| 2003/0083657 A1 | 5/2003 | Drewry et al. | |
| 2004/0138662 A1 | 7/2004 | Landry et al. | |
| 2006/0064092 A1 | 3/2006 | Howland | |
| 2006/0229615 A1* | 10/2006 | Abdou | A61B 17/8605 |
| | | | 606/279 |
| 2008/0234737 A1* | 9/2008 | Boschert | A61B 17/7008 |
| | | | 606/301 |
| 2008/0234744 A1 | 9/2008 | Zylber et al. | |
| 2009/0131982 A1* | 5/2009 | Schwab | A61B 17/7001 |
| | | | 606/279 |
| 2009/0299411 A1 | 12/2009 | Laskowitz et al. | |
| 2010/0063545 A1 | 3/2010 | Richelsoph | |
| 2010/0087865 A1 | 4/2010 | Biedermann et al. | |
| 2010/0204736 A1 | 8/2010 | Biedermann et al. | |
| 2010/0331884 A1 | 12/2010 | Hestad | |
| 2010/0331887 A1* | 12/2010 | Jackson | A61B 17/68 |
| | | | 606/279 |
| 2011/0009906 A1* | 1/2011 | Hestad | A61B 17/7022 |
| | | | 606/264 |
| 2011/0029022 A1 | 2/2011 | Zehnder et al. | |
| 2012/0029568 A1* | 2/2012 | Jackson | A61B 17/702 |
| | | | 606/264 |
| 2012/0053636 A1* | 3/2012 | Schmocker | A61B 17/7022 |
| | | | 606/264 |
| 2012/0053656 A1* | 3/2012 | Chapa | H04R 25/70 |
| | | | 607/57 |
| 2012/0283779 A1 | 11/2012 | Biedermann et al. | |
| 2013/0072992 A1* | 3/2013 | Jackson | A61B 17/7007 |
| | | | 606/305 |
| 2014/0343609 A1 | 11/2014 | Friedrich et al. | |
| 2015/0351807 A1 | 12/2015 | Jackson et al. | |
| 2016/0354118 A1 | 12/2016 | Belliard et al. | |
| 2019/0015134 A1 | 1/2019 | Belliard et al. | |

FOREIGN PATENT DOCUMENTS

| | | |
|---|---|---|
| FR | 2806615 A1 | 9/2001 |
| WO | WO-2008061802 A1 | 5/2008 |

OTHER PUBLICATIONS

"U.S. Appl. No. 15/172,631, Notice of Allowance mailed Jun. 15, 2018", 10 pgs.

"U.S. Appl. No. 15/172,631, Response filed Aug. 21, 2017 to Restriction Requirement mailed Jun. 23, 2017", 6 pgs.

"U.S. Appl. No. 15/172,631, Response filed Dec. 20, 2017 to Non Final Office Action mailed Sep. 20, 2017", 11 pgs.

"U.S. Appl. No. 15/172,631, Restriction Requirement mailed Jun. 23, 2017", 6 pgs.

"U.S. Appl. No. 16/135,754, Final Office Action mailed Apr. 8, 2020", 21 pgs.

"U.S. Appl. No. 16/135,754, Non Final Office Action mailed Dec. 10, 2019", 14 pgs.

"U.S. Appl. No. 16/135,754, Preliminary Amendment filed Jan. 2, 2019", 6 pgs.

"U.S. Appl. No. 16/135,754, Response filed Mar. 10, 2020 to Non Final Office Action mailed Dec. 10, 2019", 10 pgs.

"European Application Serial No. 15290148.4, Extended European Search Report mailed Dec. 16, 2015", 13 pgs.

"European Application Serial No. 16173205.2, Extended European Search Report mailed Oct. 7, 2016", 13 pgs.

\* cited by examiner

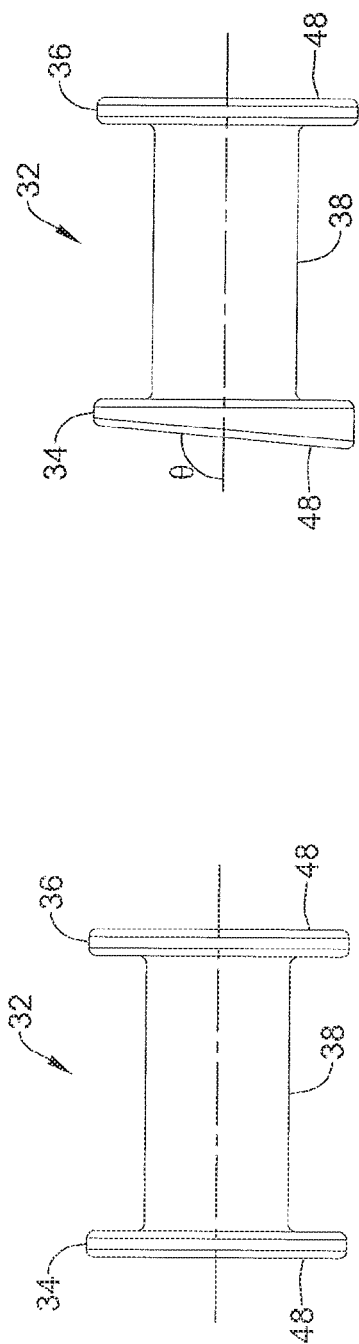
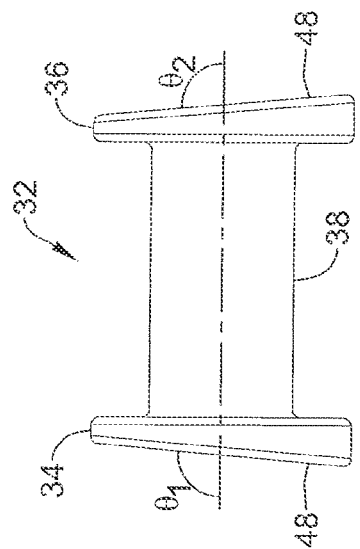
Figure 6A
Figure 6B
Figure 6C

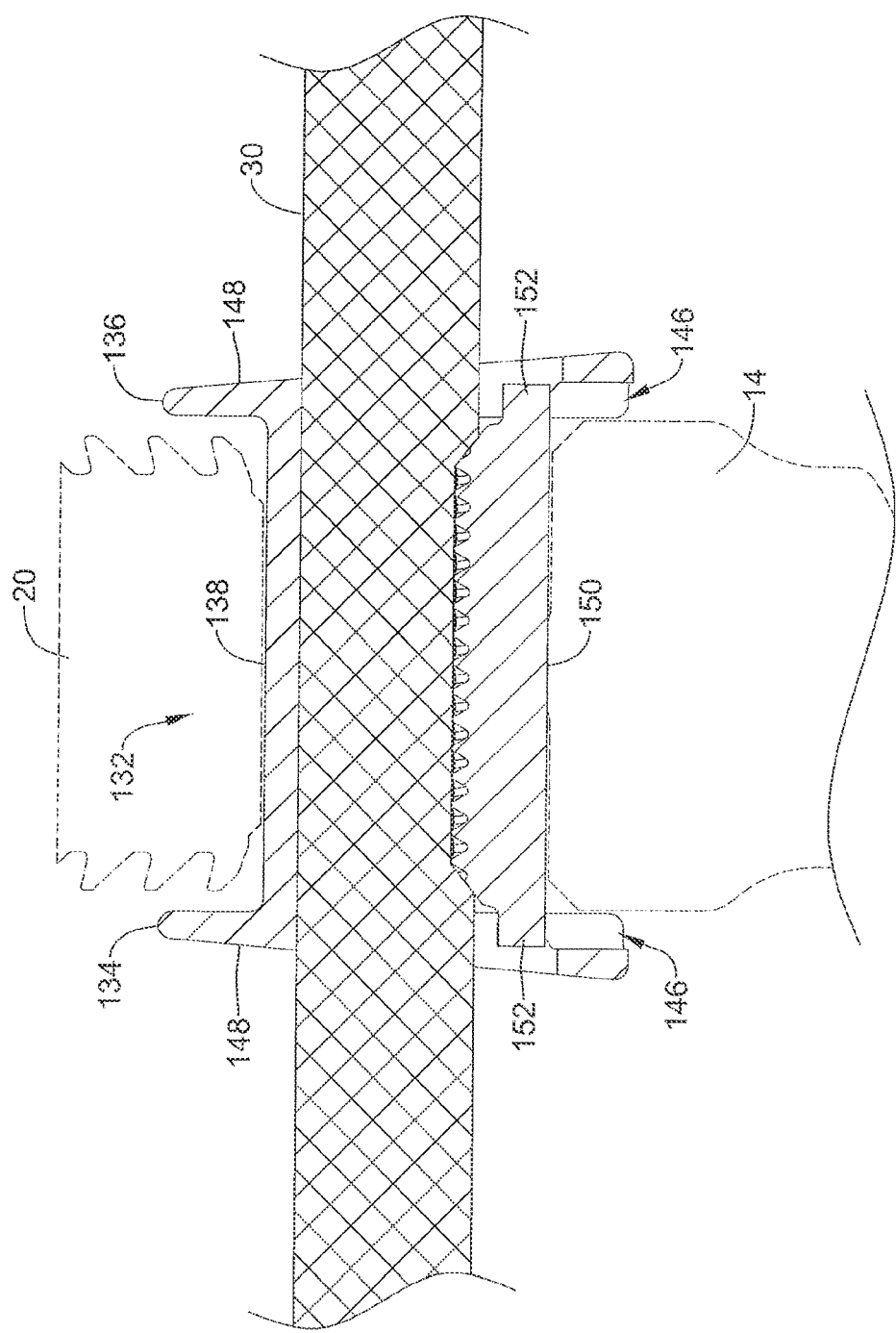

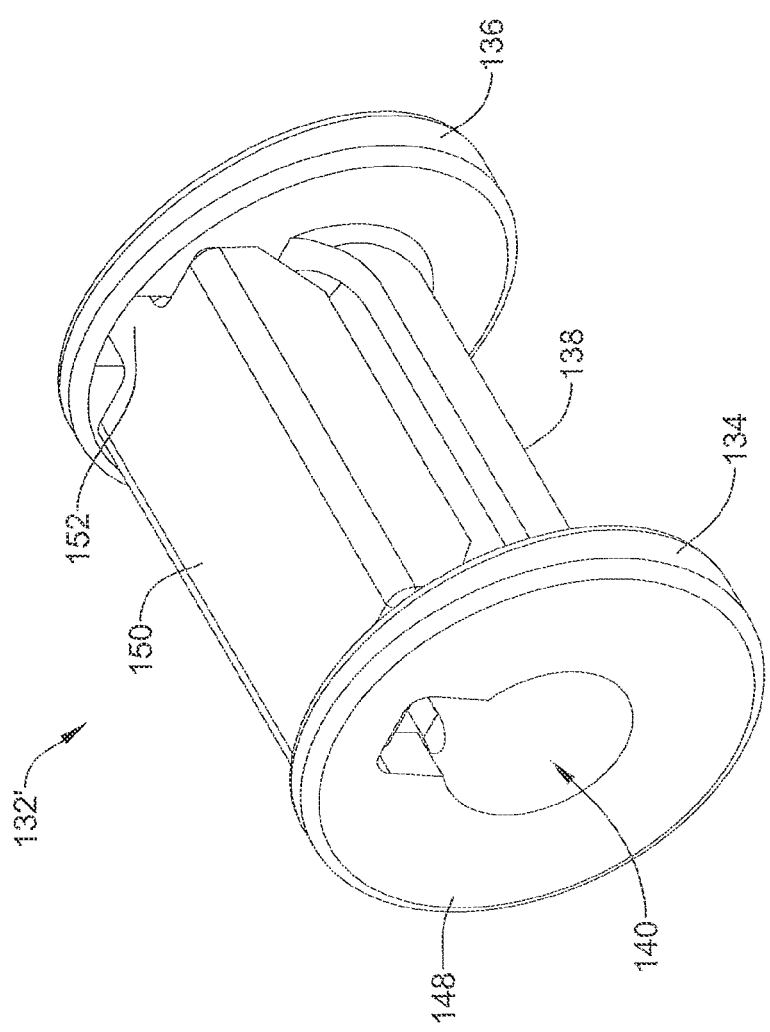

DYNAMIC SUPPORT SYSTEM

RELATED APPLICATIONS

This application is a continuation of U.S. patent application Ser. No. 16/135,754, filed on Sep. 19, 2018, which is a continuation of U.S. patent application Ser. No. 15/172,631, filed on Jun. 3, 2016, now issued as U.S. Pat. No. 10,098,670, which claims the benefit of priority to European Patent Application Serial No. 15290148.4, filed Jun. 4, 2015, the benefit of priority of each of which is claimed hereby, and each of which are incorporated by reference herein in its entirety.

TECHNICAL FIELD

The disclosure is directed to a vertebral stabilization system. More particularly, the disclosure is directed to a dynamic stabilization system and components thereof.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs can cause the patient to experience pain or discomfort and/or loss of motion, thus prompting surgery to alleviate the pain and/or restore motion of the spinal column.

One possible method of treating these conditions is to immobilize a portion of the spine to allow treatment. Traditionally, immobilization has been accomplished by rigid stabilization. For example, in a conventional spinal fusion procedure, a surgeon restores the alignment of the spine or the disc space between vertebrae by installing a rigid fixation rod between pedicle screws secured to adjacent vertebrae. Bone graft is placed between the vertebrae, and the fixation rod cooperates with the screws to immobilize the two vertebrae relative to each other so that the bone graft can fuse with the vertebrae.

Dynamic stabilization has also been used in spinal treatment procedures. Dynamic stabilization does not result in complete immobilization, but instead permits a degree of mobility of the spine while also providing sufficient support and stabilization to effect treatment. One example of a dynamic stabilization system is the Dynesys® system available from Zimmer Spine, Inc. of Minneapolis, MN. Such dynamic stabilization systems typically include a flexible member positioned between pedicle screws installed in adjacent vertebrae of the spine. A flexible cord can be threaded through the bore in the flexible member and secured to the pedicle screws while cooperating with the flexible member to permit mobility of the spine.

There is an ongoing need to provide alternative devices, assemblies, systems and/or methods that can function to alleviate pain or discomfort, provide stability, such as dynamic stability, and/or restore a range of motion to a spinal segment of a spinal column.

SUMMARY

The disclosure is directed to several alternative designs, materials and methods of manufacturing medical device structures and assemblies and uses thereof.

Accordingly, one illustrative example is a spinal stabilization system comprising an insert positionable in a channel of a housing of a vertebral anchor and a support construct including a spacer and first and second cords extendable through the spacer. The insert has a first end positionable on a first side of the housing of the vertebral anchor and a second end positionable on a second side of the housing of the vertebral anchor. The first and second cords are positionable through the insert.

Additionally or alternatively, in another example, the insert includes a first bore for receiving the first cord therethrough and a second bore for receiving the second cord therethrough.

Additionally or alternatively, in another example the system includes a vertebral anchor including a housing defining a channel and a fastener configured to rotatably engage the housing of the vertebral anchor. Rotational engagement of the fastener with the housing causes the fastener clamp both the first and second cords in the insert.

Additionally or alternatively, in another example the fastener directly contacts each of the first and second cords to exert a clamping force directly on the first and second cords.

Additionally or alternatively, in another example the fastener includes a threaded portion and a protuberance extending from the threaded portion, wherein the protuberance is extendable into an opening of the insert to contact each of the first and second cords.

Additionally or alternatively, in another example the opening intersects with each of the first and second bores.

Additionally or alternatively, in another example rotational engagement of the fastener with the housing causes the fastener clamp both the first and second cords in the insert and secure the insert in the housing of the vertebral anchor.

Additionally or alternatively, in another example the first bore extends parallel to and offset from the second bore, and the opening extends perpendicular to and between the first and second bores.

Additionally or alternatively, in another example the vertebral anchor includes a threaded shaft extending from the housing, wherein the threaded shaft has a lumen extending therethrough for advancement over a K-wire.

Additionally or alternatively, in another example the opening extends entirely through the insert such that the insert is advanceable over the K-wire into the housing of the vertebral anchor with the K-wire positionable between the first and second cords.

Another illustrative example is a spinal stabilization system including an insert securable to a housing of a vertebral anchor, a support construct including a spacer and a cord extendable through the spacer, and a clamping member. The insert has a first flange positionable on a first side of the housing of the vertebral anchor, a second flange positionable on a second side of the housing of the vertebral anchor, and a medial portion between the first and second flanges positionable in a channel of the housing of the vertebral anchor. The cord is positionable through a bore of the insert. The clamping member is movable relative to the medial portion to clamp the cord in the bore of the insert.

Additionally or alternatively, in another example the clamping member includes a concave engagement surface configured to press against a portion of the periphery of the cord, preferably 30 degrees or more of the periphery of the cord.

Additionally or alternatively, in another example the clamping member includes a first tab movable in a channel in the first flange and a second tab movable in a channel in the second flange.

Additionally or alternatively, in another example the clamping member is configured to be held in a loading position prior to clamping onto the cord.

Additionally or alternatively, in another example each of the channels has an upper portion having a first width and a lower portion having a second width, the first width being less than the width of the first and second tabs to form an interference fit with the first and second tabs, and the second width being greater than the width of the first and second tabs.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIGS. 6A through 6C illustrate exemplary configurations of an insert of a spinal stabilization system;

FIG. 10C is a longitudinal cross-sectional view of the insert of FIG. 7 in an alternate orientation within a vertebral anchor;

FIG. 11A is a perspective view of another exemplary insert of a spinal stabilization system;

Figure 1:
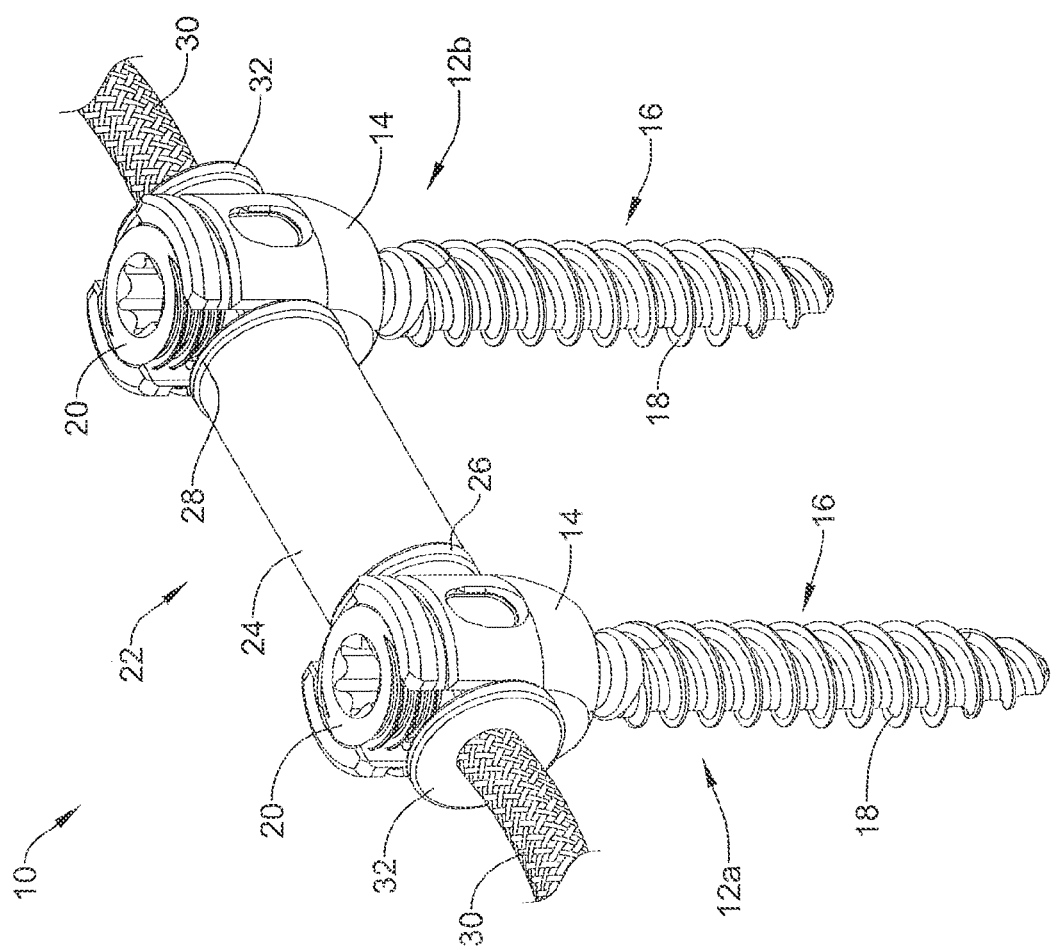
FIG. 1 is a perspective view of an exemplary spinal stabilization system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, there is shown a spinal fixation system 10 for stabilizing a portion of a spinal column, such as one or more spinal segments of a spinal column. As used herein, a spinal segment is intended to refer to two or more vertebrae, the intervertebral disc(s) between the vertebrae and other anatomical elements between the vertebrae. For example, a spinal segment can include first and second adjacent vertebrae and the intervertebral disc located between the first and second vertebrae. The spinal stabilization system 10 can provide dynamic stabilization to a spinal segment, preserving and/or allowing for a range of motion of the spinal segment.

In some embodiments, the spinal stabilization system 10 can be used to treat discogenic low back pain, degenerative spinal stenosis, disc herniations, facet syndrome, posterior element instability, adjacent level syndrome associated with spinal fusion, and/or other maladies associated with the spinal column.

The spinal stabilization system 10 can include one or more or a plurality of vertebral anchors, depicted as pedicle screws 12. However, in some embodiments the vertebral anchors can be vertebral hooks (e.g., laminar hooks) or other types of fastening members for attachment to a bony structure such as a vertebra of the spinal column. Each of the pedicle screws 12 can be configured to be secured to a vertebra of a spinal column. For instance, the first pedicle screw 12a can be secured to a first vertebra and the second pedicle screw 12b can be secured to a second vertebra. Additional pedicle screws 12 can be present in instances in which the spinal stabilization system 10 spans three or more vertebra of the spinal column.

Figure 2:
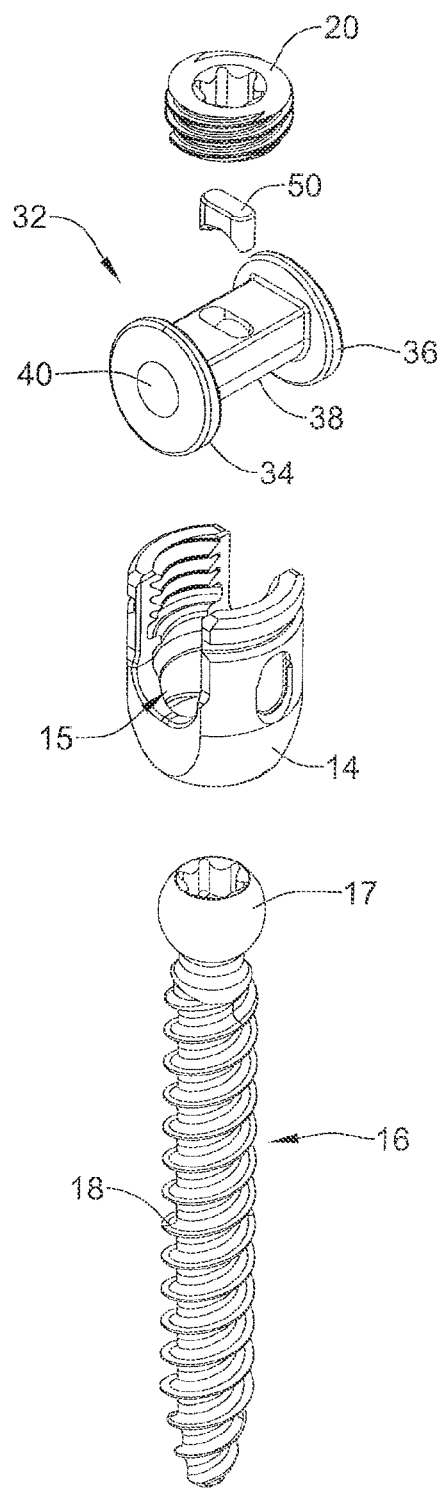
FIG. 2 is an exploded perspective view of components of the spinal stabilization system of FIG. 1, including an insert positionable in a the channel of the housing of the pedicle screw.

The pedicle screw 12 can include a housing 14 and a shaft 16, which can include threads 18, extending from the housing 14. The housing 14 can include a channel, such as a U-shaped channel extending from one side of the housing 14 to an opposite second side of the housing 14. The channel 15 (see FIG. 2) can be defined between opposing legs of the housing 14. The shaft 16 can be configured to be installed into a bony region of a vertebra of the spinal column. For example, the shaft 16 can be installed into a pedicle of a vertebra, or other region of a vertebra. The shaft 16 can extend along a longitudinal axis. The pedicle screw 12 depicted in the Figures is a poly-axial pedicle screw which allows the housing 14 to be pivotable relative to the shaft 16 to a plurality of angular positions relative to the longitudinal axis. The pedicle screw 12, as shown in FIG. 2, can include a head portion 17 at the end of the shaft 16 which is received in the housing 14. The housing 14 can be pivotable relative to the head portion 17 of the shaft 16. In other instances, the pedicle screw 12 can be mono-axial or mono-planar, if desired.

The pedicle screw 12 can include a securing element, such as a threaded fastener 20 (e.g., a set screw, cap) configured to rotatably engage the housing 14 to secure a portion of a support construct 22 to the pedicle screw 12. For example, the threaded fastener 20 can include threads which mate with threads formed in the housing 14. In other embodiments, the fastener 20 can include one or more flanges, cam surfaces, or other engagement features that engage with one or more channels, grooves, surfaces, or other engagement features of the housing 14 through rotation of the fastener 20. The fastener 20 can be rotatably engaged between spaced apart legs of the housing 14 which define the channel 15 of the housing 14 therebetween.

The spinal stabilization system 10 can also include one or more, or a plurality of support constructs 22 extending between pedicle screws 12 of the spinal stabilization system 10. As an illustrative example, the spinal stabilization system 10 shown in FIG. 1 includes a support construct 22 extending between the first pedicle screw 12a and the second pedicle screw 12b.

The support construct 22 can be constructed of a plurality of components in some instances. For instance, the support construct 22 can include a spacer 24, and a flexible member such as a flexible cord 30 extending through the spacer 24, as well as other components if desired.

In some embodiments, the spacer 24 can be an annular spacer having a lumen (not shown) extending from a first end 26 to a second end 28 of the spacer 24. For example, in some embodiments the spacer 24 can be a cylindrical member having a lumen extending therethrough. In other embodiments, the spacer 24 can be molded, extruded, or otherwise formed over and/or around the cord 30. The spacer 24 can be positioned between the housing 14 of the first pedicle screw 12a and the housing 14 of the second pedicle screw 12b. In some embodiments, the spacer 24 can be formed from polycarbonate urethane (PCU), although it will be recognized that various other materials suitable for implantation within the human body and for providing stabilization of the spine while maintaining flexibility can be used. In other embodiments, the spacer 24 can be constructed of other materials such as metal, polymeric materials, or combinations of materials.

The cord 30 can extend from the housing 14 of the first pedicle screw 12a to the housing 14 of the second pedicle screw 12b. In one embodiment, the cord 30 can be formed from polyethylene-terephthalate (PET), although it will be recognized that various other materials suitable for implantation within the human body and for providing stabilization of the spine while maintaining flexibility can be used. In other embodiments, the cord 30 can be constructed of other flexible materials such as metal, polymeric materials, or combinations of flexible materials. It is noted that during a medical procedure the portions of the cord 30 which are shown extending from the channels of the pedicle screws 12a, 12b can be trimmed as desired to reduce and/or eliminate the portion of the cord 30 extending from the pedicle screws 12a, 12b.

When implanted in a patient, the cord 30 of the spinal stabilization system 10 can limit the range of flexion of the spinal segment, whereas the spacer 24 can limit the range of extension of the spinal segment. For instance, the cord 30 can be placed in tension and the spacer 24 can be placed in compression between the pedicle screws 12a, 12b.

The spinal stabilization system 10 can also include inserts 32 configured to be inserted into the channels 15 of the housings 14 of the pedicle screws 12. One possible embodiment of the insert 32 is further illustrated in FIGS. 3 and 4. The inserts 32, which can be considered spools in some instances, can include a first flange 34 proximate a first end of the insert 32, a second flange 36 proximate the second end of the insert 32, and a medial portion 38 intermediate the first flange 34 and the second flange 36 and extending therebetween. The insert 32 can have end surfaces 48 configured to abut an end surface of the spacer 24. For instance, when assembled an end surface 48 of an insert 32 coupled with the first pedicle screw 12a can abut an end surface of the spacer 24 proximate the first end 26 of the spacer 24 and an end surface 48 of an insert 32 coupled with the second pedicle screw 12b can abut an end surface of the spacer 24 proximate the second end 28 of the spacer 24.

The insert 32 can be configured such that the medial portion 38 is positionable in the channel 15 (shown in FIG. 2) of the housing 14 of the pedicle screw 12 with the first flange 34 positioned exterior of the housing 14 and facing the first side of the housing 14 and the second flange 36 positioned exterior of the housing 14 and facing the second side of the housing 14. The insert 32 can be positioned in the channel 15 in a top-loaded fashion in which the insert 32 is moved into the channel 15 of the housing 14 in a direction generally perpendicular to the longitudinal axis of the channel 15 of the housing 14.

The insert 32 can include bore 40 extending from a first end surface 48 at the first end of the insert 32 to a second end surface 48 at the second end of the insert 32 along a longitudinal axis through the insert 32. The bore 40 can be configured to receive the cord 30 therein. For instance, the cord 30 can be inserted into and/or through the bore 40 of the insert 32. Thus, the cord 30 can extend out of the bore 40 from the first end surface 48 at the first end of the insert 32 in a first direction and/or the cord 30 can extend out of the bore 40 from the second end surface 48 at the second end of the insert 32 in a second direction opposite the first direction.

Figure 3:
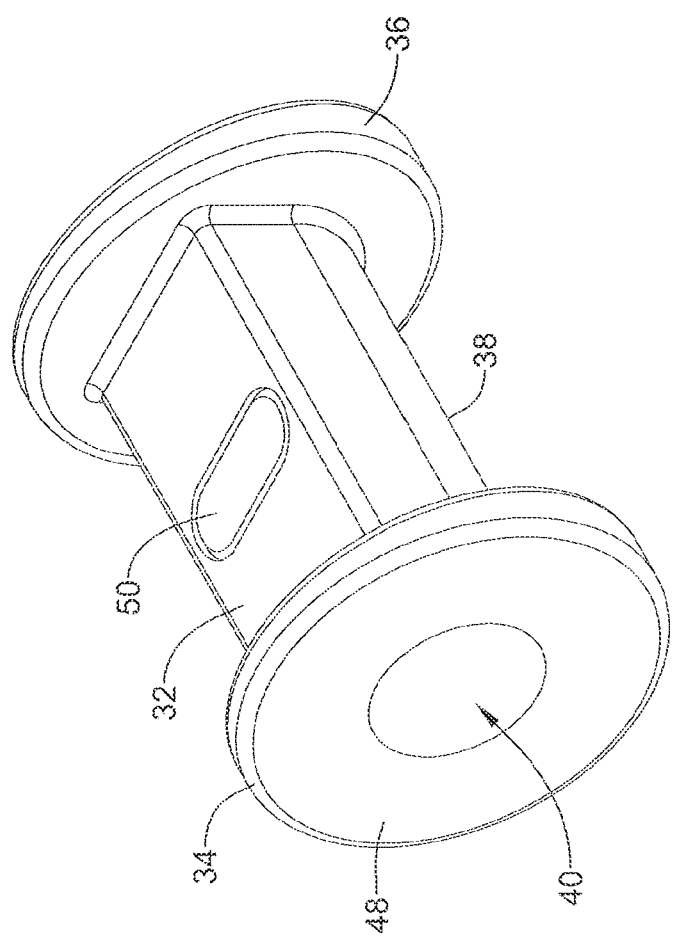
FIG. 3 is a perspective view of the insert of spinal stabilization system of FIG. 1.
Figure 4:
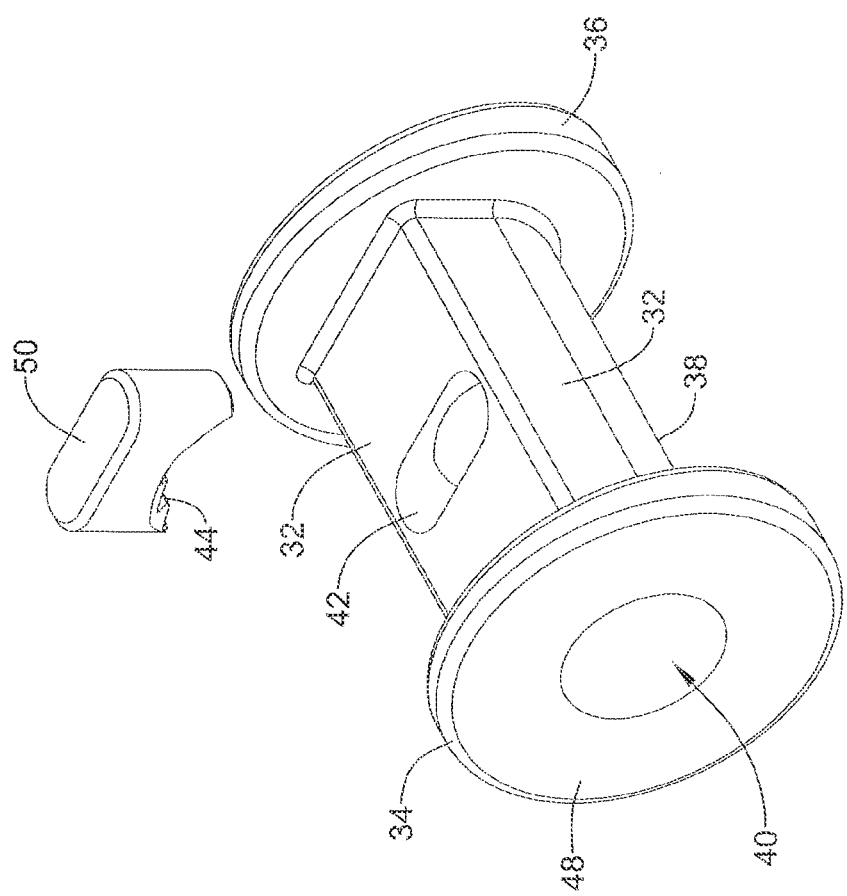
FIG. 4 is an exploded perspective view of the insert of FIG. 3.

The insert 32 can include a clamping member 50 configured to clamp or secure the cord 30 within the bore 40 of the insert 32. For example, the clamping member 50 can be inserted into an opening 42 in the medial portion 38 of the insert 32 to bear against the cord 30. The opening 42 can intersect with the bore 40 to provide direct engagement of the clamping member 50 with a portion of the cord 30 positioned in the bore 40. In some instances, the insert 32 can be press fit in the opening 42. As shown in FIG. 3, in some instances, the clamping member 50 can be inserted into the opening 42 until the exterior surface of the clamping member 50 is flush with an exterior surface of the medial portion 38 of the insert 32.

Figure 5A:
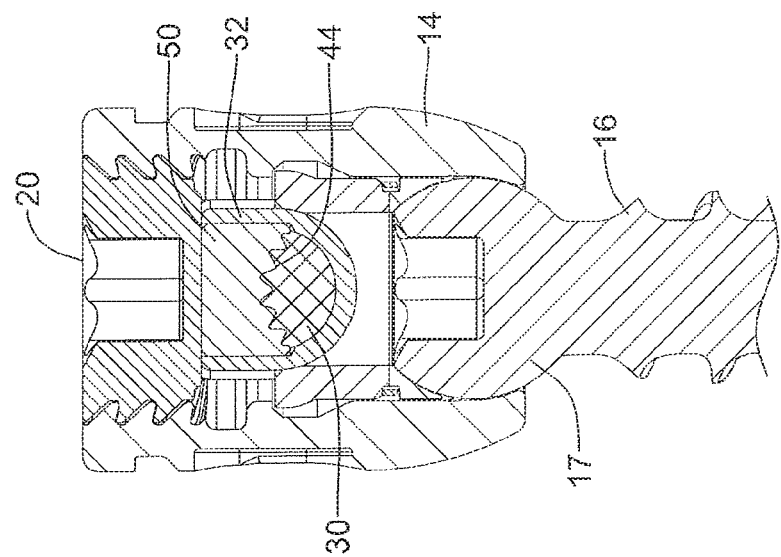
FIG. 5A is a cross-sectional view of the insert positioned in the housing of the pedicle screw of the spinal stabilization system prior to securement of the insert in the housing.

The clamping member 50 can include any mechanical gripping means such as, but not limited to, one or more ribs, projecting grooves, teeth, posts, spikes, and/or serrations or combination thereof for engaging and/or penetrating into the cord 30. In the illustrated embodiment, the clamping member 50 can include a generally concave engagement surface 44 having a plurality of ribs, teeth, serrations, grooves, or other gripping features formed along the concave surface 44, configured to engage and/or penetrate into the cord 30. As shown in FIG. 5A, the concave engagement surface 44 can be configured to engage the periphery of the cord 30, such as 30 degrees or more, 45 degrees or more, 60 degrees or more, 75 degrees or more, or 90 degrees or more around the periphery (e.g., circumference) of the cord 30 when engaging the cord 30 in the bore 40.

In some instances, the cord 30 can be pre-assembled with the insert 32 and secured in the bore 40 with the clamping member 50 by pressing the clamping member 50 against the cord 30 prior to inserting the insert 32 into the channel 15 of the housing 14 of the pedicle screw 12. Additionally or alternatively, the cord 30 can be intra-operatively secured in the bore 40 with the clamping member 50 while securing the insert 32 in the channel 15 of the housing 14 of the pedicle screw 12 with the fastener 20.

Figure 5B:
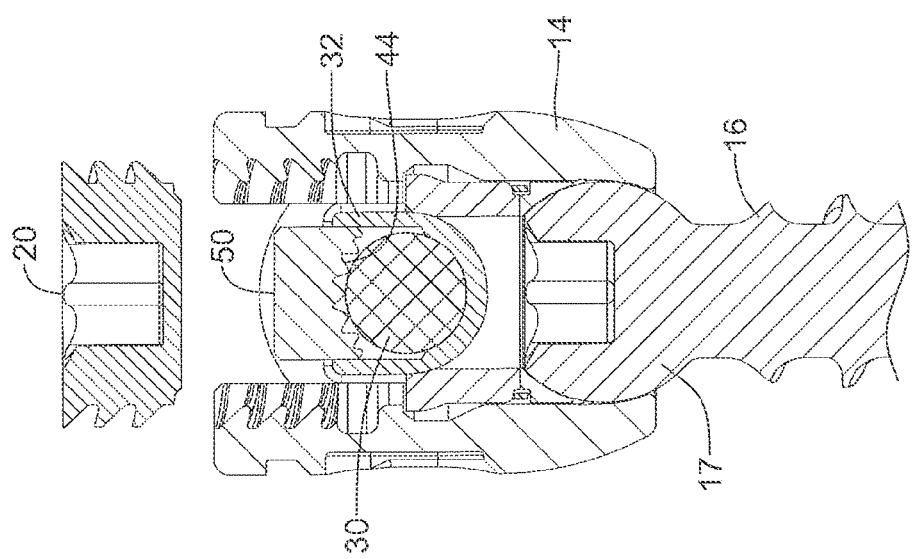
FIG. 5B is a cross-sectional view of the insert secured in the housing of the pedicle screw of the spinal stabilization system.

One exemplary configuration for securing the cord 30 in the bore 40 while simultaneously locking the housing 14 of the poly-axial pedicle screw 12 from pivotal movement is shown in FIGS. 5A and 5B.

As shown in FIG. 5A, the insert 32 can be inserted into the channel 15 of the housing 14 in a direction generally perpendicular to the longitudinal axis of the bore 40. The cord 30, extending into or through the bore 40 of the insert 32, can also be inserted into the channel 15 of the housing 14 with the cord 30 extending from the first side of the housing 14 and/or extending from the second side of the housing 14. Thus, the medial portion 38 of the insert 32 can be positioned within the U-shaped channel 15.

The fastener 20 can then be engaged with the housing 14, such as through rotational movement of the fastener 20 relative to the housing 14. In some instances, the fastener 20 can include a threaded portion which threadably engages a threaded portion of the housing 14, such as internally threaded portions of opposing legs of the housing 14 defining the channel 15. Rotational movement of the fastener 20 moves the fastener 20 into engagement with the insert 32.

As shown in FIG. 5B, rotational engagement of the fastener 20 with the housing 14 causes the fastener 20 to directly contact the clamping member 50 to exert a force on the clamping member 50 to push the clamping member 50 toward the cord 30. The amount of rotation of the fastener 20, and thus axial movement of the fastener 20 along its axis of rotation, controls the displacement of the clamping member 50 in the opening 42 toward the cord 30. The concave surface 44 of the clamping member 50 can contact a portion of the periphery (e.g., circumference) of the cord 30, such as 5% or more, 10% or more, 15% or more, 20% or more, or 25% or more of the periphery of the cord 30. Deformation of the cord 30 and/or penetration into the cord 30 by the clamping member 50 can prevent the cord 30 from moving axially through the bore 40 of the insert 32.

In some instances, the clamping force generated through rotational engagement of the fastener 20 with the housing 14 both clamps the cord 30 to the insert 32 (and thus secures the cord 30 to the pedicle screw 12) and locks the housing 14 from pivotal movement relative to the shaft 16 of the pedicle screw 12. For instance a locking force exerted by the fastener 20 can be transmitted through the insert 32 to the head portion 17 of the shaft 16 to lock the housing 14 from pivotable movement relative to the head portion 17 of the shaft 16. When the clamping force is sufficiently large, the clamping force exerted onto the head portion 17 by the insert 32 locks the housing 14 from pivotal movement relative to the head portion 17.

As shown in FIGS. 6A-6C, the end surfaces 48 of the insert 32 can be oriented at any desired angle relative to the longitudinal axis of the bore 40 extending through the insert 32. For example, in FIG. 6A, the both the first and second end surfaces 48 of the insert 32 can be generally perpendicular to the longitudinal axis of the bore 40. In other instances, one or more of the end surfaces 48 can be oriented at an oblique angle to the longitudinal axis of the bore 40, such as for use in lordotic applications. For example, in FIG. 6B, the first end surface 48 of the insert 32 can be at an oblique angle $\theta$ to the longitudinal axis of the bore 40, while the second end surface 48 of the insert can be generally perpendicular to the longitudinal axis of the bore 40. Alternatively, in FIG. 6C, the first end surface 48 of the insert 32 can be at an oblique angle $\theta_1$ to the longitudinal axis of the bore 40 and the second end surface 48 of the insert 32 can be at an oblique angle $\theta_2$ to the longitudinal axis of the bore 40. The angles $\theta_1$ and $\theta_2$ can be the same or different. The angles $\theta_1$, $\theta_2$ and/or $\theta$ can be any desired angle, such as 2°, 3°, 4°, 5°, 6°, 7°, 8°, 9° or 10°, for example. It is note that any of the embodiments of an insert described herein can include end surfaces which are perpendicular and/or oblique to the longitudinal axis of the bore extending through the insert.

Figure 7:
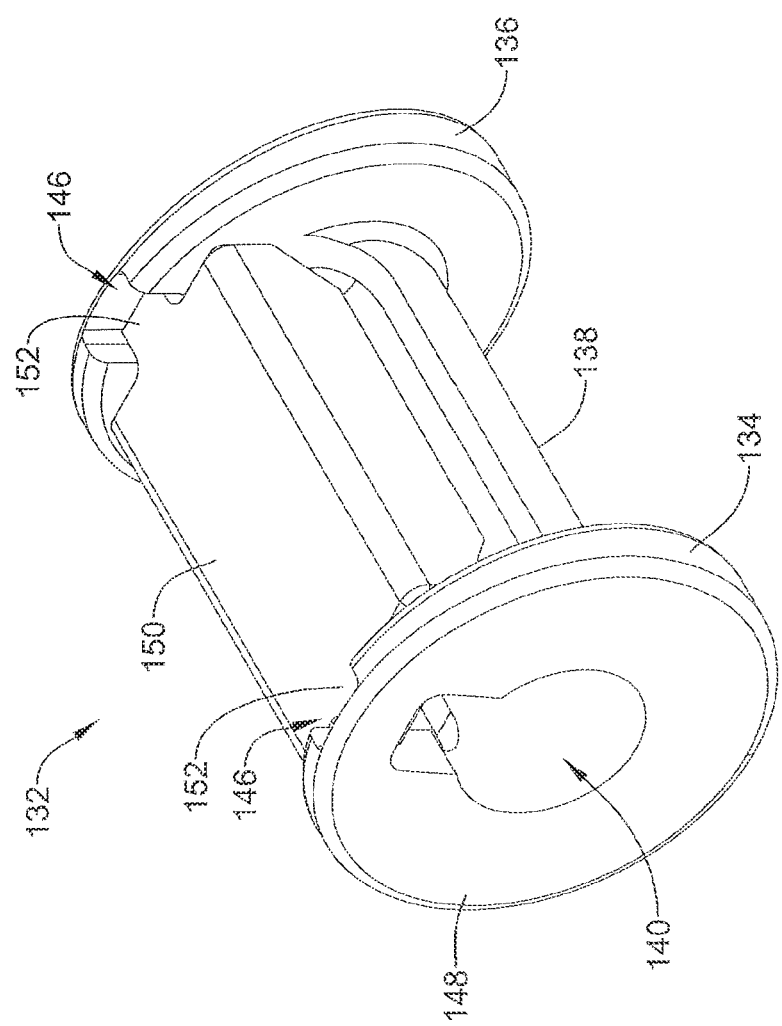
FIG. 7 is a perspective view of another exemplary insert of a spinal stabilization system.
Figure 8:
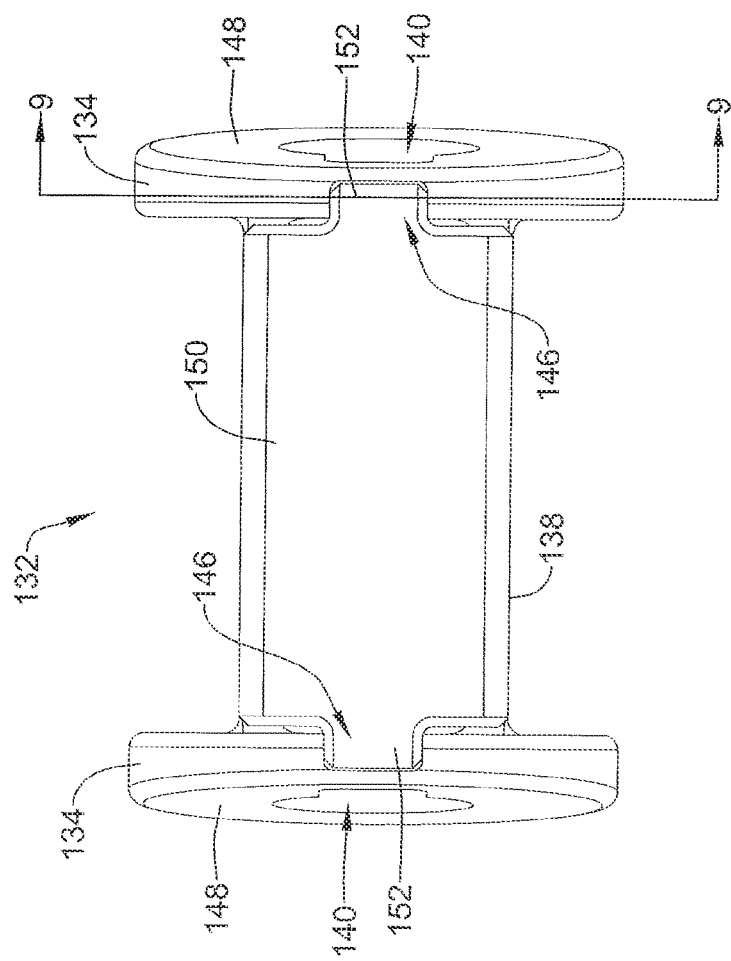
FIG. 8 is a top view of the insert of FIG. 7.
Figure 9:
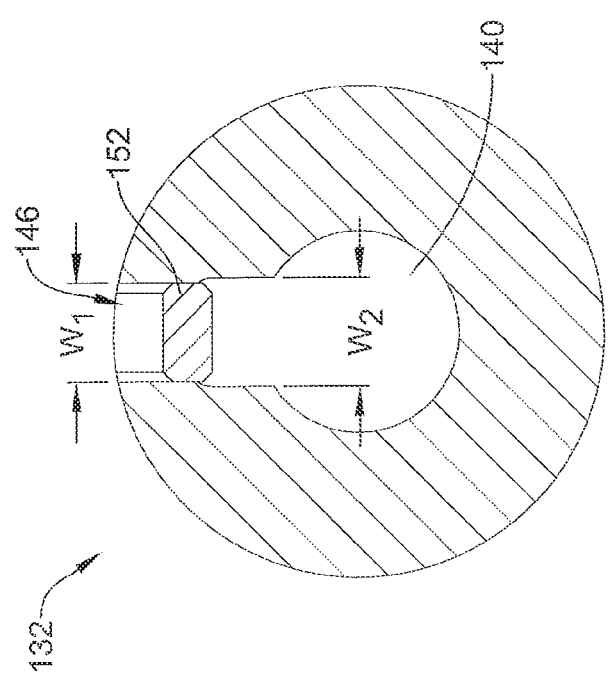
FIG. 9 is a cross-sectional view of the insert taken along line 9-9 of FIG. 8.

Another embodiment of an insert 132 configured for securement of the cord 30 within the housing 14 of a pedicle screw 12 or other vertebral anchor is illustrated in FIGS. 7-9. The insert 132 can be similar to the insert 32 in many respects. For example, the insert 132 can include a first flange 134 proximate a first end of the insert 132, a second flange 136 proximate the second end of the insert 132, and a medial portion 138 intermediate the first flange 134 and the second flange 136 and extending therebetween. The insert 132 can have end surfaces 148 configured to abut an end surface of the spacer 24. The insert 132 can be configured such that the medial portion 138 is positionable in the channel 15 of the housing 14 of the pedicle screw 12 with the first flange 134 positioned exterior of the housing 14 and facing the first side of the housing 14 and the second flange 136 positioned exterior of the housing 14 and facing the second side of the housing 14.

The insert 132 can include bore 140 extending from a first end surface 148 at the first end of the insert 132 to a second end surface 148 at the second end of the insert 132 along a longitudinal axis through the insert 132. The bore 140 can be configured to receive the cord 30 therein.

Figure 10A:
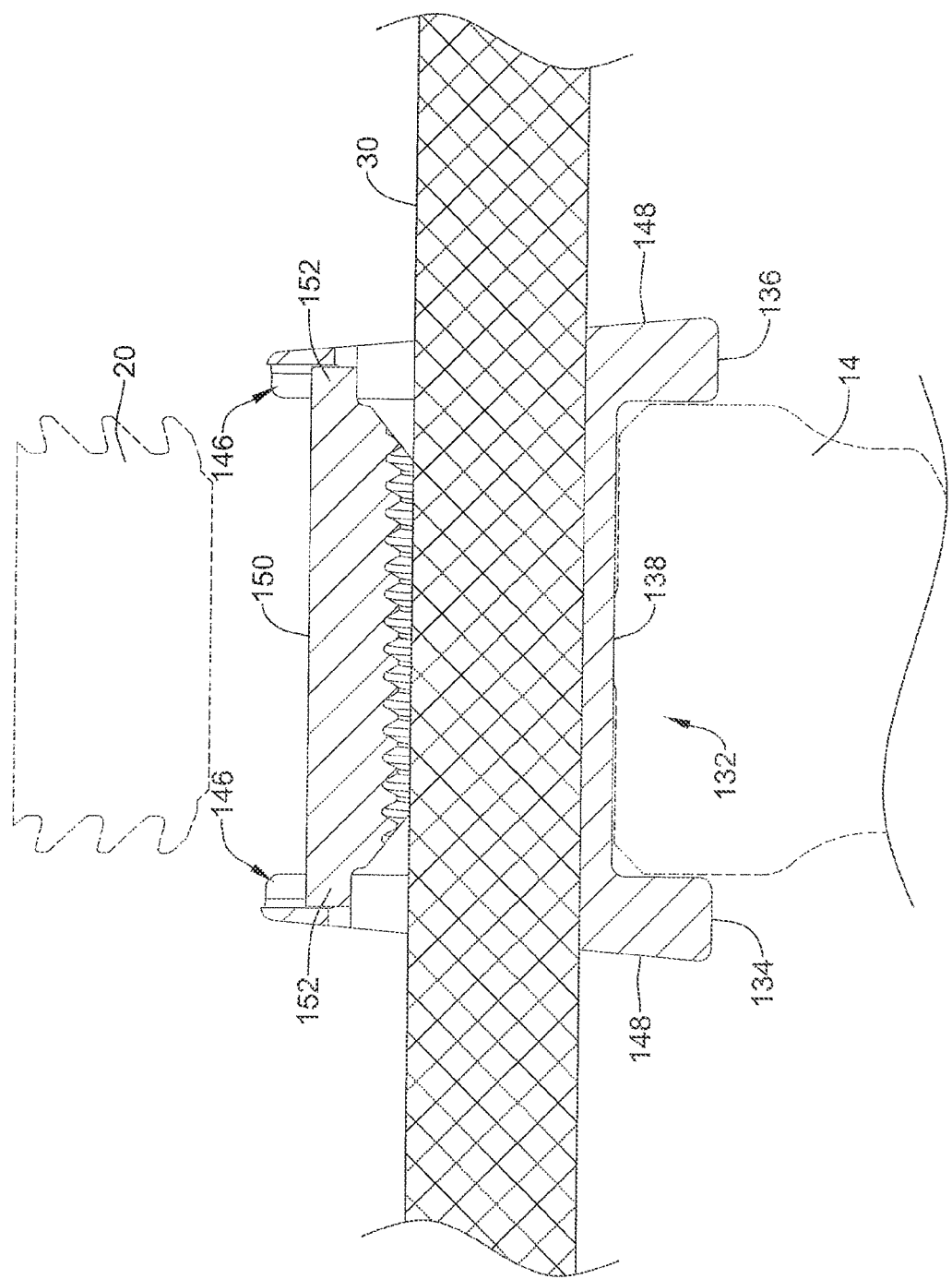
FIGS. 10A and 10B are longitudinal cross-sectional views of the insert of FIG. 7 while securing a flexible cord within the insert.

The insert 132 can include a clamping member 150 configured to clamp or secure the cord 30 within the bore 140 of the insert 132. For example, the clamping member 150 can be movable relative to the medial portion 138 of the insert 132 to bear against the cord 30 and clamp the cord 30 therebetween. The clamping member 150 can include a first tab 152 extending into a channel 146 in the first flange 134 and a second tab 152 extending into a channel 146 in the second flange 136. The tabs 152 can move along the channels 146 as the clamping member 150 is moved toward the cord 30 to clamp the cord 30 in the bore 140. In some instances, such as shown in FIG. 8, the tabs 152 can form an interference fit with the channels 146 such that walls of the tabs 152 frictionally engage walls of the channels 146 to resist movement of the clamping member 150 relative to the medial portion 138 of the insert 132 unless and until the force sufficient to overcome the frictional/interference force is overcome. As shown in FIG. 9, in some instances the upper portion of the channels 146 can have a width $W_1$ and a lower portion of the channels 146 can have a width $W_2$ greater than the width $W_1$. The tabs 152 can have a width greater than the width $W_1$ to provide an interference fit in the upper portion of the channel 146. However, the width of the tabs 152 can be less than the width $W_2$ of the lower portion of the channel 146. Thus, as shown in FIG. 10A, the clamping member 150 can be initially positioned in a first, loading position with the tabs 152 forming an interference fit in the upper portion of the channel 146, retaining the clamping member 150 in the loading position such that the clamping member 150 does not interfere with positioning the cord 30 into and/or through the bore 140 of the insert 132. Upon applying sufficient force to the clamping member 150 to overcome the frictional force (e.g., tightening the fastener 20 in the housing 14 of the pedicle screw 12 to apply a force against the clamping member 150), the tabs 152 move into the wider lower portion of the channel 146 to the clamped position, shown in FIG. 10B, with the clamping member 150 engaging and/or penetrating into the cord 30 to secure the cord 30 in the bore 140 of the insert 132.

It is noted that other configurations are contemplated for initially holding the clamping member 150 in a loading position to facilitate positioning the cord 30 in the bore 140. For example, detents can be incorporated with the tabs 152/channels 146 to form an interference between the components.

The clamping member 150 can include any mechanical gripping means such as, but not limited to, one or more ribs, projecting grooves, teeth, posts, spikes, and/or serrations or combination thereof for engaging and/or penetrating into the cord 30. In the illustrated embodiment of FIGS. 10A-10C, the clamping member 150 can include a generally concave engagement surface having a plurality of ribs, teeth, serrations, grooves, or other gripping features formed along the concave surface, configured to engage and/or penetrate into the cord 30. The concave engagement surface can be configured to engage the periphery of the cord 30, such as 30 degrees or more, 45 degrees or more, 60 degrees or more, 75 degrees or more, or 90 degrees or more around the periphery (e.g., circumference) of the cord 30 when engaging the cord 30 in the bore 140.

Figure 10B:
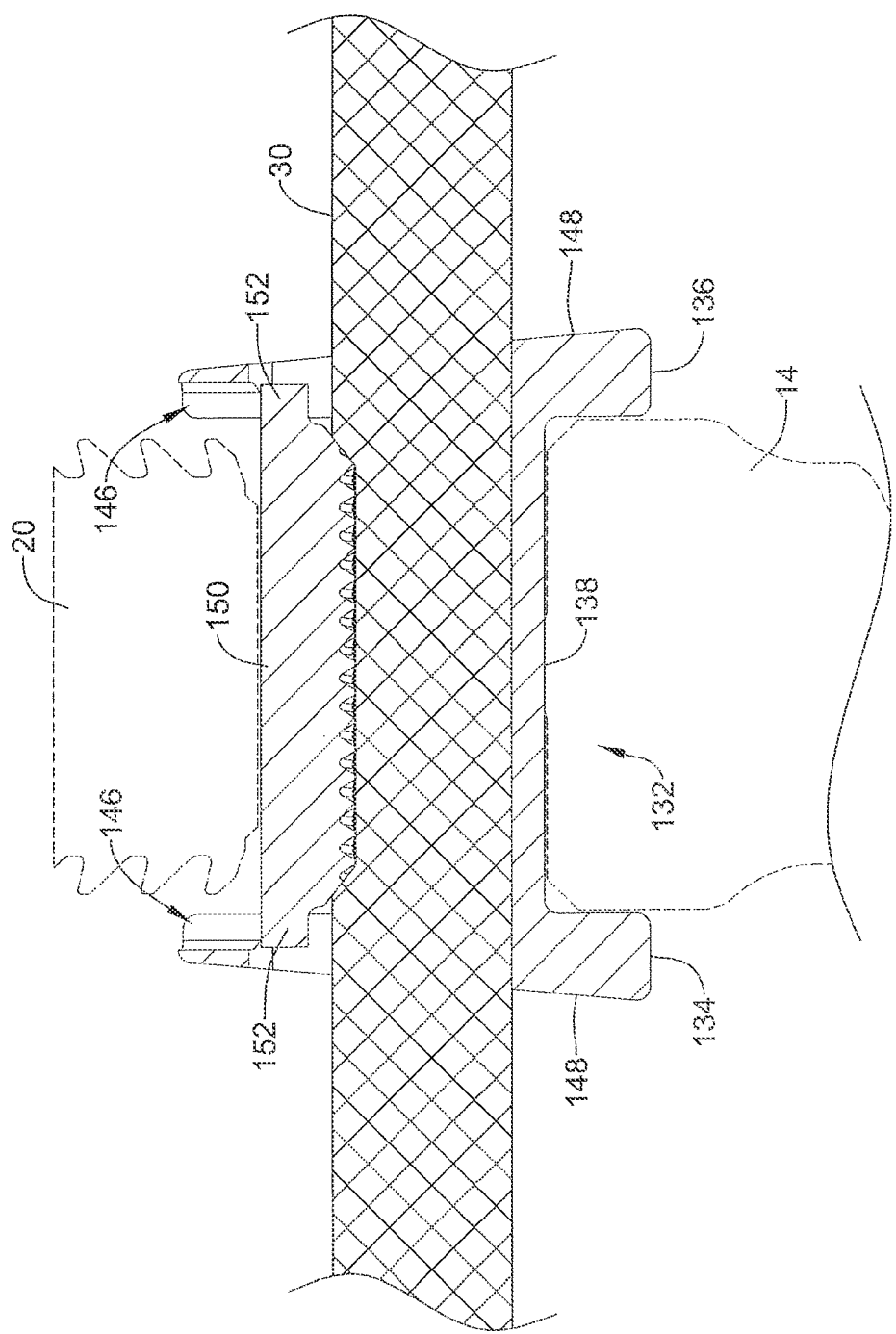

Additionally or alternatively to the embodiment of FIGS. 10A-10C, the medial portion 138 of the insert 132 can include any mechanical gripping means such as, but not limited to, one or more ribs, projecting grooves, teeth, posts, spikes, and/or serrations or combination thereof for engaging and/or penetrating into the cord 30. In the illustrated embodiment of FIG. 12B, the medial portion 138 can include a generally concave engagement surface having a plurality of ribs, teeth, serrations, grooves, or other gripping features formed along the concave surface, configured to engage and/or penetrate into the cord 30. The concave engagement surface can be configured to engage the periphery of the cord 30, such as 30 degrees or more, 45 degrees or more, 60 degrees or more, 75 degrees or more, or 90 degrees or more around the periphery (e.g., circumference) of the cord 30 when engaging the cord 30 in the bore 140.

In some instances, the cord 30 can be pre-assembled with the insert 132 and secured in the bore 140 with the clamping member 150 by pressing the clamping member 150 against the cord 30 prior to inserting the insert 132 into the channel 15 of the housing 14 of the pedicle screw 12. Additionally or alternatively, the cord 30 can be intra-operatively secured in the bore 140 with the clamping member 150 while securing the insert 132 in the channel 15 of the housing 14 of the pedicle screw 12 with the fastener 20.

FIG. 10C illustrates another possible orientation of the insert 132 positioned in the channel of the housing 14 of a pedicle screw (shown in phantom). As shown in FIG. 10C, in some instances the insert 132 can be positioned in the channel of the housing 14 of the pedicle screw 12 with the clamping member 150 below or distal the medial region 138 of the insert 132, with the flanges 134, 136 positioned on opposite sides of the housing 14, if desired. Upon applying sufficient force to the clamping member 150 to overcome the frictional force between the tabs 152 and channels 146 (e.g., tightening the fastener 20 in the housing 14 of the pedicle screw 12 to apply a force against the medial region 138), the medial region 138 and first and second flanges 134, 136 move downward relative to the housing 14 to clamp the cord 30 between the medial region 138 and clamping member 150. As the medial region 138 and flanges 134, 136 move relative to the housing 14 and clamping member 150, the tabs 152 move into the wider lower portion of the channel 146 to the clamped position, with the clamping member 150 engaging and/or penetrating into the cord 30 to secure the cord 30 in the bore 140 of the insert 132. Accordingly, in some instances the fastener 20 can bear against the medial region 138 of the insert 132 while the clamping member 150 can bear against a component of the housing 14, for example.

Figure 11B:
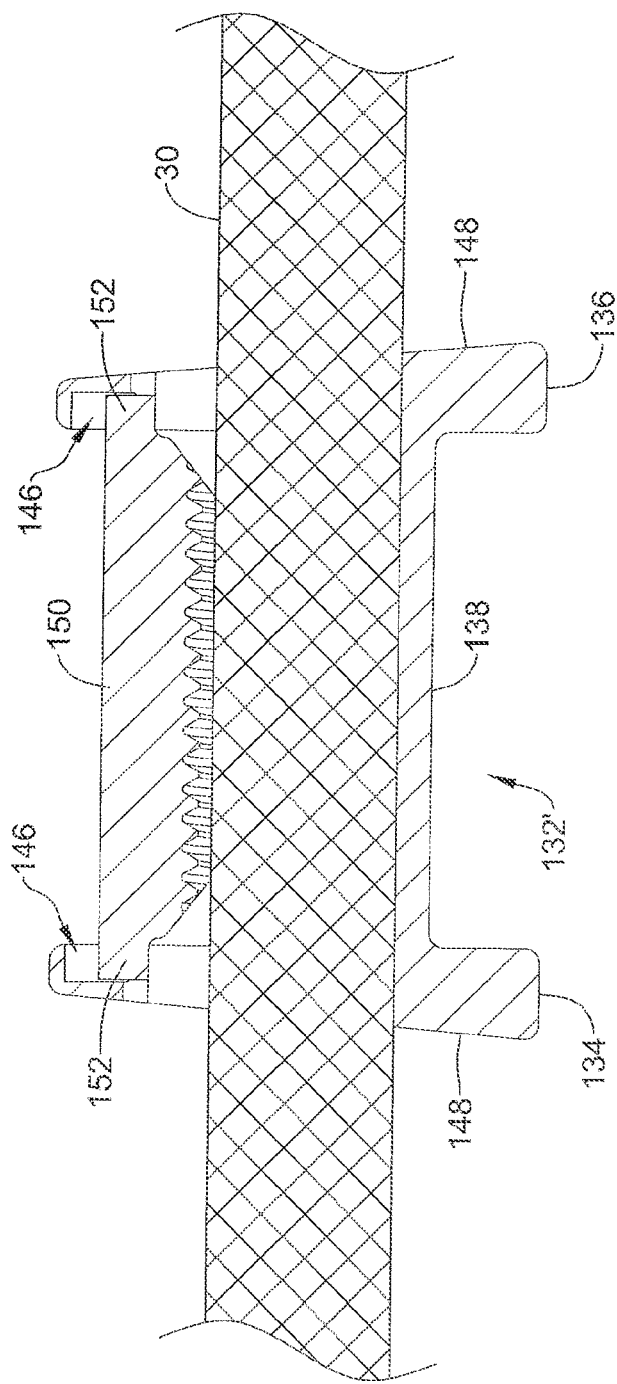
FIG. 11B is a longitudinal cross-sectional view of the insert of FIG. 11A.
Figure 12A:
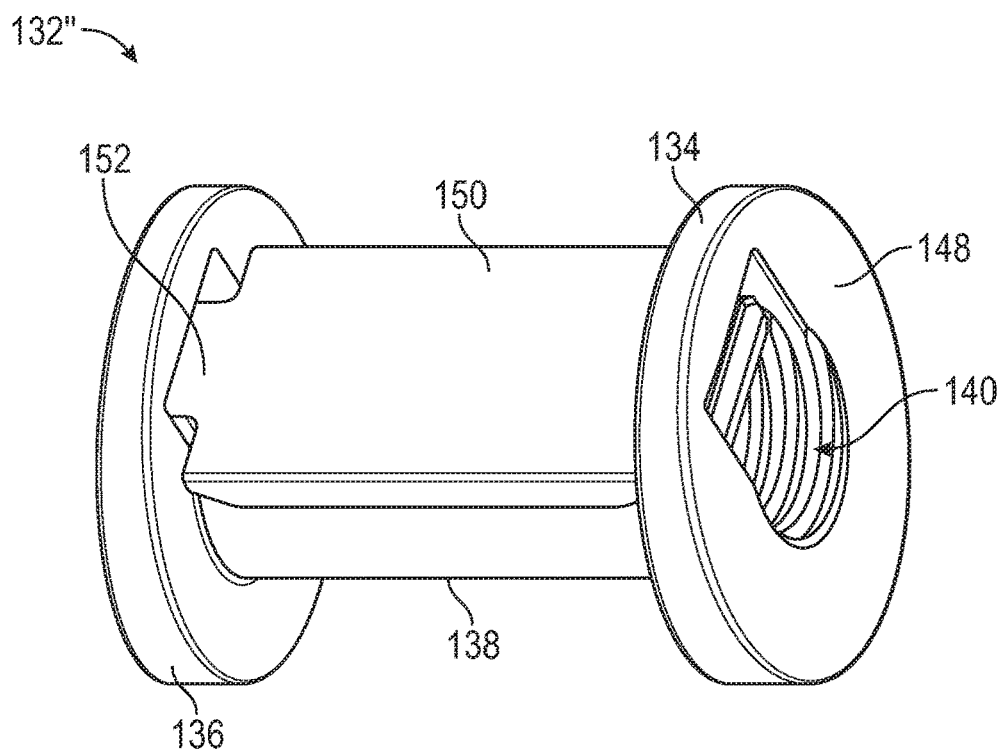
FIG. 12A is a perspective view of another exemplary insert of a spinal stabilization system.
Figure 12B:
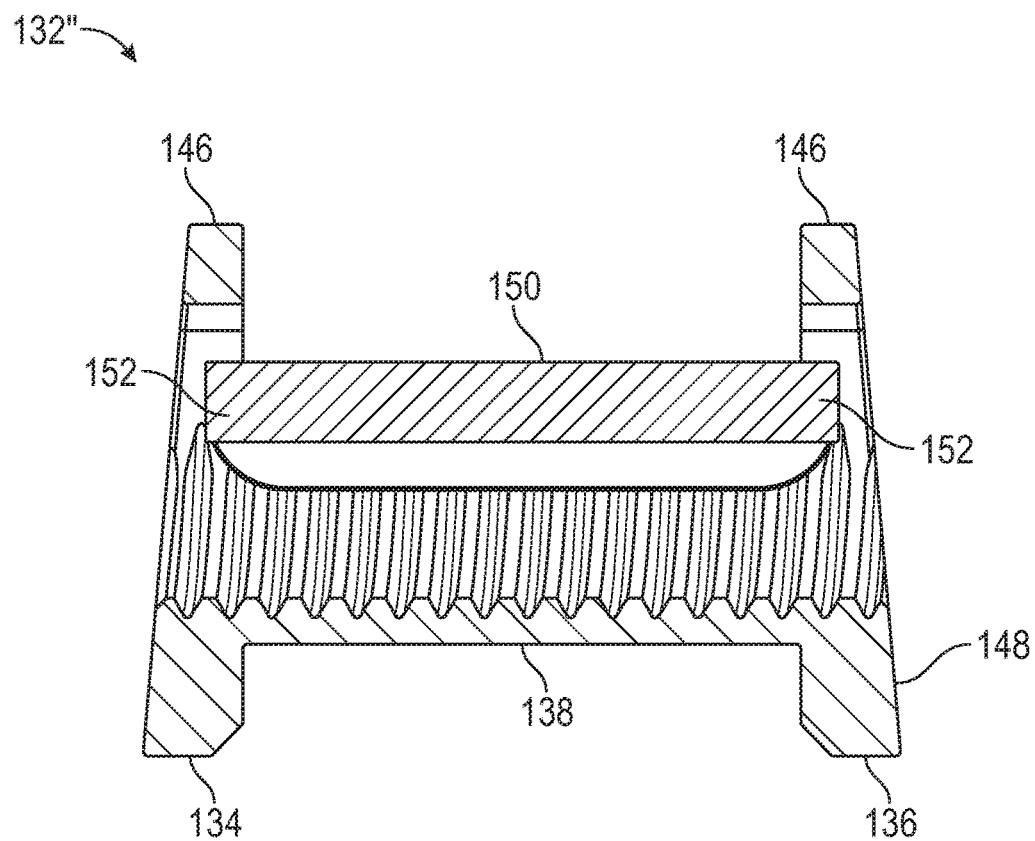
FIG. 12B is a perspective view of another exemplary insert of a spinal stabilization system.

FIGS. 11A and 11B illustrate insert 132', which is a variation of the insert 132. Unlike the embodiment of FIGS. 7-8, in which the channels 146 extend to the outer peripheral edge of the flanges 134, 136, in the variation of FIGS. 11A and 11B, the channels 146 may not extend to the outer peripheral edge of the flanges 134, 136. Such an embodiment can help retain the clamping member 150 assembled with the main body of the clamping member 150 during assembly of the construct. FIGS. 12A and 12B illustrate insert 132", which is a variation of the insert 132' illustrating that the width of the channels 146 and tabs 152 can be up to about the diameter of the bore 140.

Figure 13A:
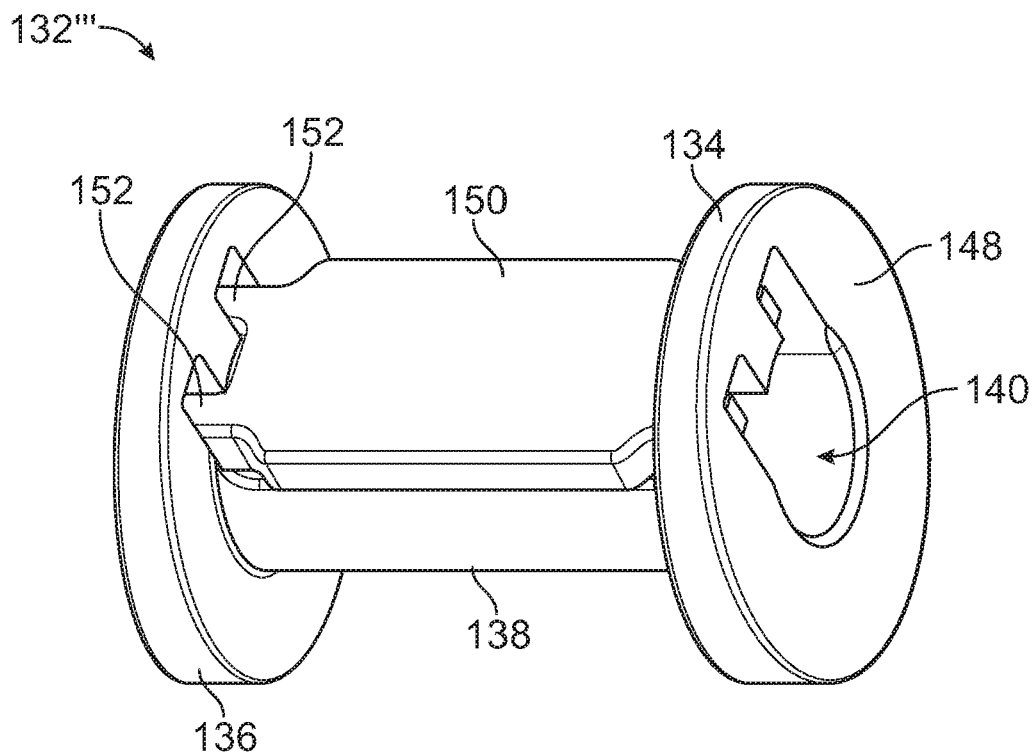
FIG. 13A is a perspective view of another exemplary insert of a spinal stabilization system.
Figure 13B:
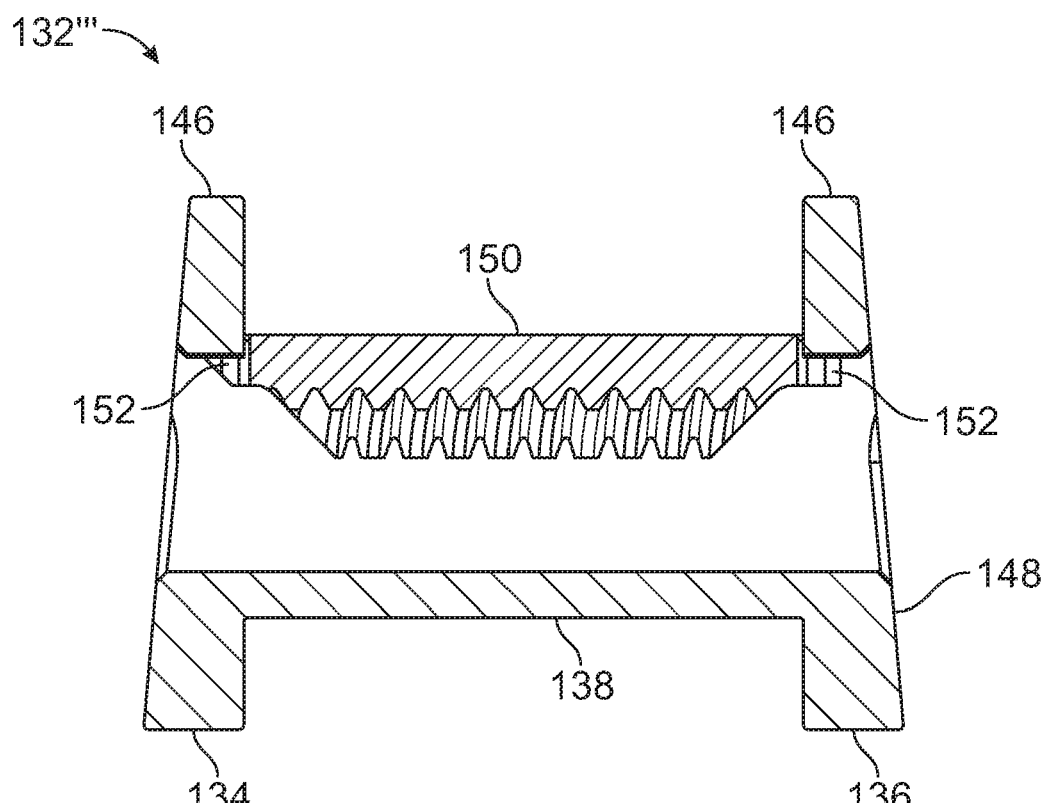
FIG. 13B is a perspective view of another exemplary insert of a spinal stabilization system.
Figure 14:
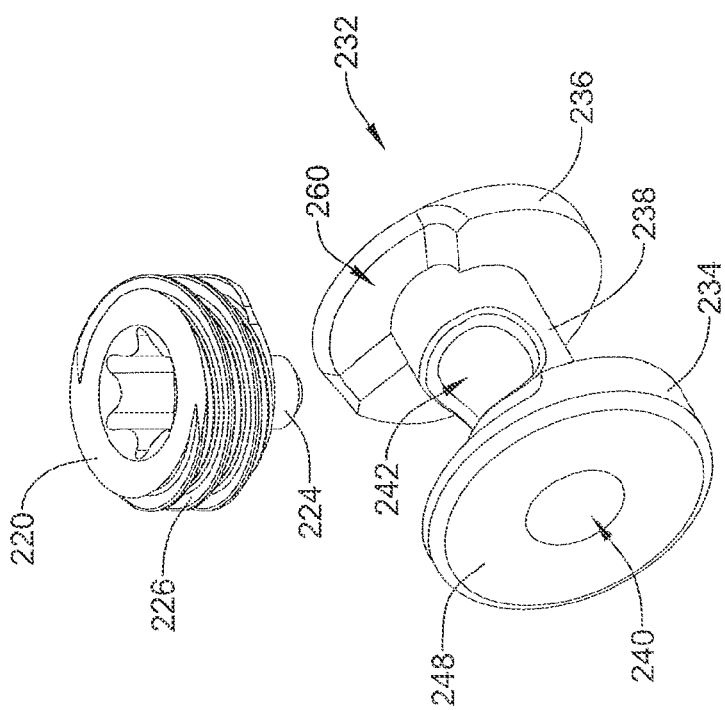
FIG. 14 is a perspective view of another exemplary insert and associated locking member of a spinal stabilization system.

FIGS. 13A and 13B illustrate insert 132', which is a variation of the insert 132". Unlike the embodiment of FIGS. 12A-12B, in which the channels 146 and tabs 152 each have a uniform width, in the variation of FIGS. 13A and 13B, the upper portion of the channels 146 can have a protuberance extending radially towards the bore 140 and the tabs 152 can have a void disposed therein that receives the protuberance in mating engagement.

It is noted that in other instances, the insert 132, 132' can include channels at opposing ends of the clamping member 150 configured to mate with and receive projections extending into the channels from the flanges 134, 136. In other instances, the insert 132, 132' can include a channel at a first end of the clamping member 150 configured to mate with and receive a projection extending into the channels from one of the flanges 134, 136 and a tab extending from the opposite, second end of the clamping member 150 configured to mate with and extend into a channel in the other of the flanges 134, 136.

Another embodiment of an insert 232 configured for securement of the cord 30 within the housing 14 of a pedicle screw 12 or other vertebral anchor is illustrated in FIG. 13. The insert 232 can be similar to the insert 32 in many respects. For example, the insert 232 can include a first flange 234 proximate a first end of the insert 232, a second flange 236 proximate the second end of the insert 232, and a medial portion 238 intermediate the first flange 234 and the second flange 236 and extending therebetween. The insert 232 can have end surfaces 248 configured to abut an end surface of the spacer 24. The insert 232 can be configured such that the medial portion 238 is positionable in the channel 15 of the housing 14 of the pedicle screw 12 with the first flange 234 positioned exterior of the housing 14 and facing the first side of the housing 14 and the second flange 236 positioned exterior of the housing 14 and facing the second side of the housing 14.

The insert 232 can include bore 240 extending from a first end surface 248 at the first end of the insert 232 to a second end surface 248 at the second end of the insert 232 along a longitudinal axis through the insert 232. The bore 240 can be configured to receive the cord 30 therein.

The insert 232 can include an opening 242 in the medial portion 238 of the insert 232 for receiving a clamping member to bear against the cord 30. The opening 242 can intersect with the bore 240 to provide direct engagement of the clamping member with a portion of the cord 30 positioned in the bore 240. The clamping member can be a fastener 220, such as a threaded set screw including threads which mate with threads formed in the housing 14. The fastener 220 can be rotatably engaged between spaced apart legs of the housing 14 to apply a clamping force to the cord 30 to clamp or secure the cord 30 within the bore 240 of the insert 232 while simultaneously clamping the insert 232 in the housing 14 of a pedicle screw 12. For example, the fastener 220 can include a threaded portion 226 and a protuberance 224 extending from the threaded portion 226. The protuberance 224 can extend into the opening 242 to bear against the cord 30 and clamp the cord 30 in the bore 240.

Figure 16:
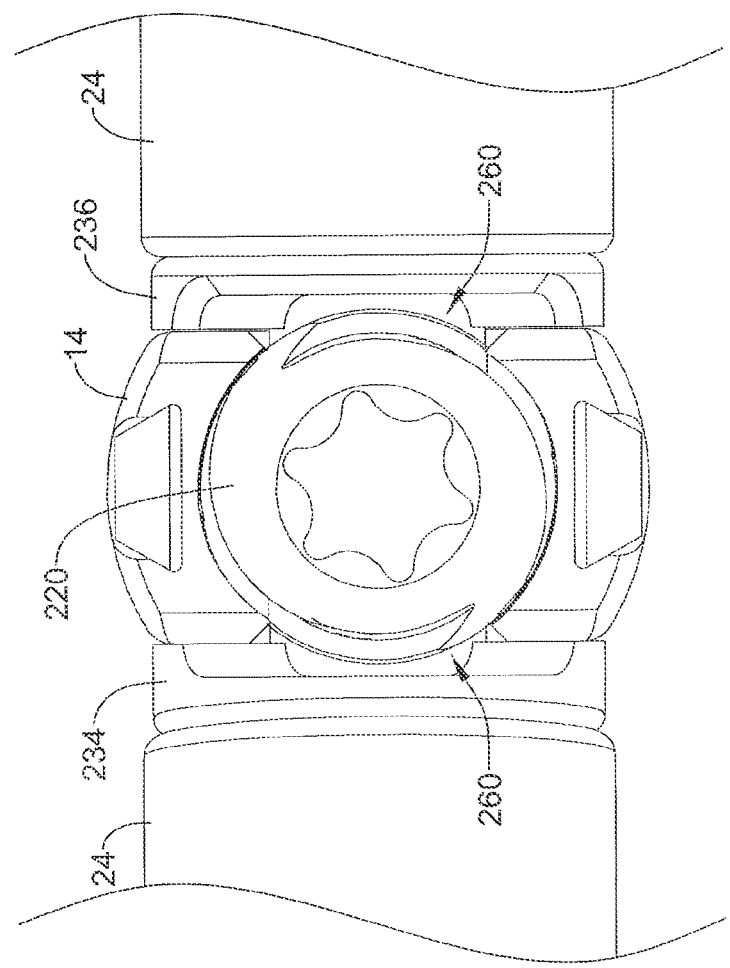
FIG. 16 is a top view of a portion of the spinal stabilization system of FIG. 15.

The insert 232 can also include recesses 260 formed in the flanges 234, 236 of the insert 232 to accommodate the fastener 220 therebetween. For instance, as shown in FIG. 16, the fastener 220 can have an outer diameter greater than the distance between the first flange 234 and the second flange 236 (i.e., the distance between the inner surfaces of the flanges 234, 236 facing the medial portion 238. Thus, the recesses 260 can provide clearance for the fastener 220 to be rotatably engaged with the housing 14 of the pedicle screw 12 between the first and second flanges 234, 236. Furthermore, the recesses 260 can allow for a degree of rotational variability of the insert 232 (about the longitudinal axis of the bore 240) relative to the housing 14 when positioning and securing the insert 232 in the housing 14.

Figure 15:
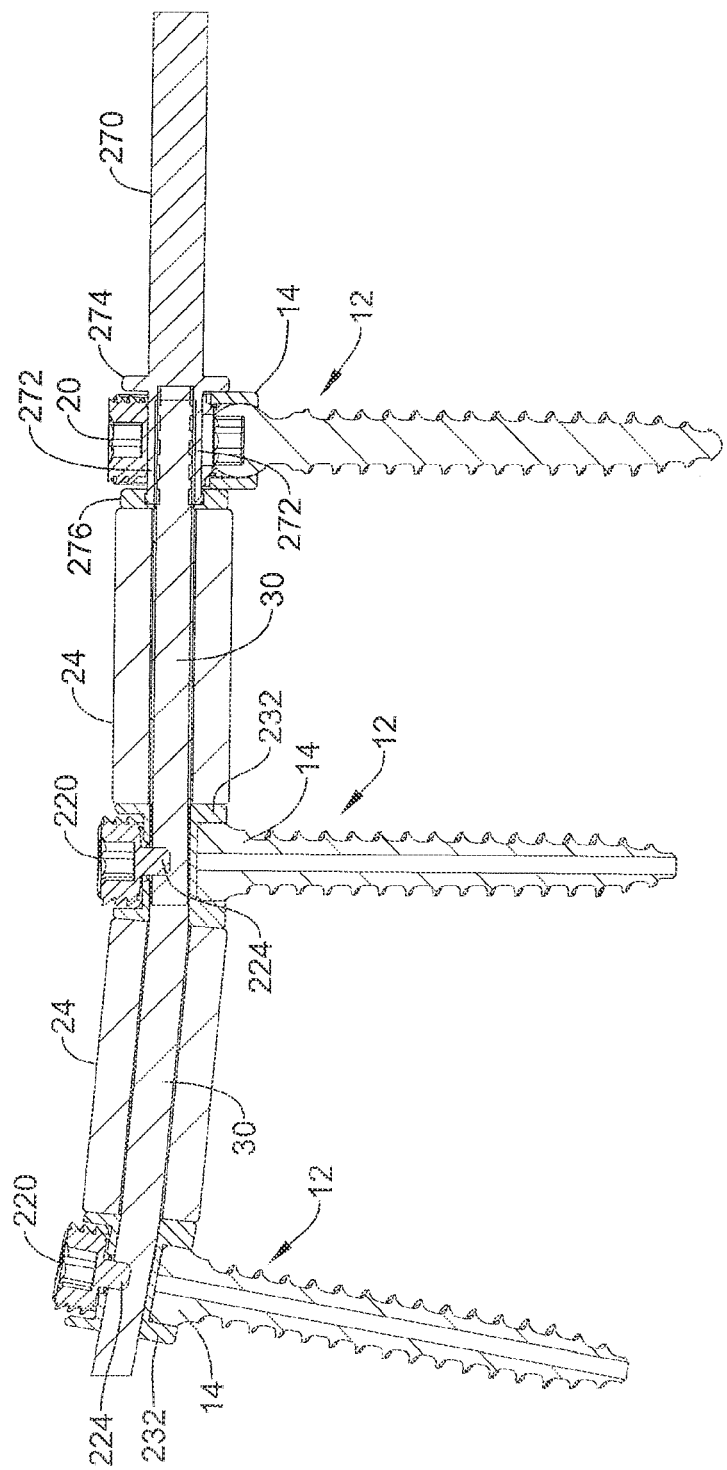
FIG. 15 is a longitudinal cross-sectional view of a spinal stabilization system utilizing inserts as shown in FIG. 14.

FIG. 15 illustrates a support construct 222 utilizing inserts 232. The support construct 222 can also include spacers 24 and a flexible member such as a flexible cord 30 extending through the spacers 24, as well as other components if desired. The inserts 232 are shown positioned in the housing 14 of the pedicle screws 12, with spacers 24 positioned between facing surfaces of the inserts 232. The flexible cord 30 can extend through the bores 240 of the inserts 232 and the lumen of the spacers 24. The fasteners 220 can be threadably engaged with the housing 14 of the pedicle screws 12 to secure the inserts 232 to the housing 14 while the protuberance 224 of the inserts 232 can simultaneously engage the cord 30 to secure the cord 30 relative to the insert 232 and housing 14.

Furthermore, the end of the cord 30 can be secured to a rigid rod member 270, providing a transition between the dynamic or flexible portion of the construct 222 and a rigid portion of the construct 222. The rigid rod 270 can extend to one or more additional pedicle screws (not shown), for example.

The rigid rod member 270 can include an end region configured to be secured to an end region of the cord 30. For example, end region of the rigid rod member 270 can be configured as a clam shell connector having a plurality of segments 272 collectively defining a bore for receiving the end region of the cord 30. The segments 272 can extend from a flange 274 of the rigid rod member 270 positionable on a first side of the housing 14 of the pedicle screw 12. The free ends of the segments 272 can move toward one another (e.g., radially inward toward the central longitudinal axis of the cord 30 to clamp around the cord 30. For example, a clamping force can be exerted on the segments 272 to move the free ends toward one another. A retaining ring 276 can be slid over the cord 30 and placed around the free ends of the segments 272 to secure the cord 30 and prevent the free ends of the segments 272 from separating. The segments 272 of the clam shell connector can be positioned in the channel of the housing 14 of the pedicle screw 12 with the flange 274 on a first side of the housing 14 and the retaining ring 276 on a second, opposite side of the housing 14. The retaining ring 276 can act as a flange for engagement with a spacer 24 of the support construct 222.

Figure 17:
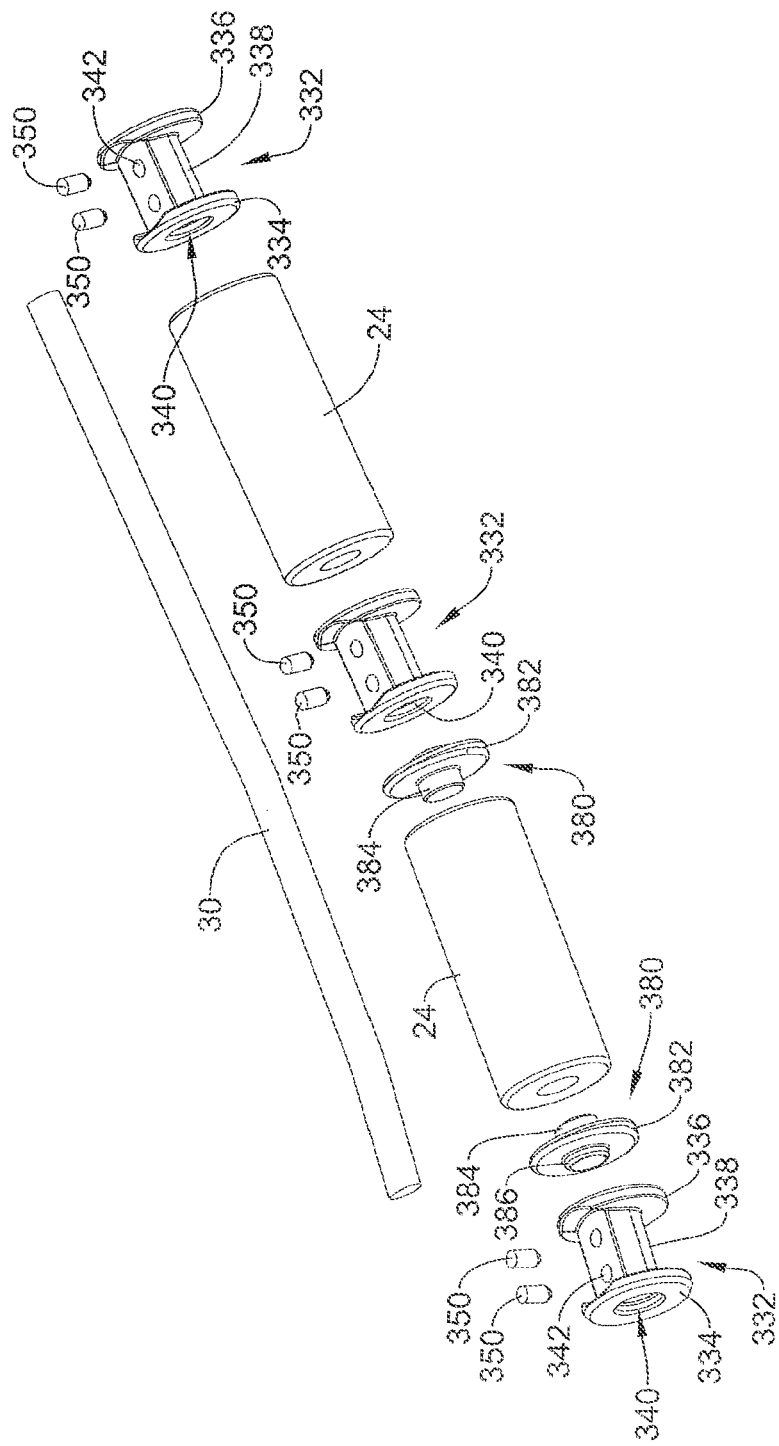
FIG. 17 is an exploded view of components of another spinal stabilization system.

Components of another exemplary support construct 322 utilizing inserts 332 are shown in FIG. 17. It is noted that the inserts 332 can be substituted with any other configuration of insert described herein, if desired. The support construct 322 includes inserts 332 for securement in the housings 14 of pedicle screws 12 or other vertebral anchors, as well as spacers 24 and a flexible member such as a flexible cord 30 extending through the spacers 24 and secured in the inserts 332.

The inserts 332 can be similar to the other inserts 332 described herein in many respects. For example, the inserts 332 can include a first flange 334 proximate a first end of the insert 332, a second flange 336 proximate the second end of the insert 332, and a medial portion 338 intermediate the first flange 334 and the second flange 336 and extending therebetween. The insert 332 can be configured such that the medial portion 338 is positionable in the channel 15 of the housing 14 of the pedicle screw 12 with the first flange 334 positioned exterior of the housing 14 and facing the first side of the housing 14 and the second flange 336 positioned exterior of the housing 14 and facing the second side of the housing 14.

The insert 332 can include bore 340 extending from a first end surface at the first end of the insert 332 to a second end surface at the second end of the insert 332 along a longitudinal axis through the insert 332. The bore 340 can be configured to receive the cord 30 therein.

The insert 332 can include one or more, or a plurality of openings 342 in the medial portion 338 of the insert 332 for receiving a clamping member to bear against the cord 30. The openings 342 can intersect with the bore 340 to provide direct engagement of the clamping member with a portion of the cord 30 positioned in the bore 340. The clamping members can be pins 350 press fit, or otherwise positioned in the openings 342.

Figure 19:
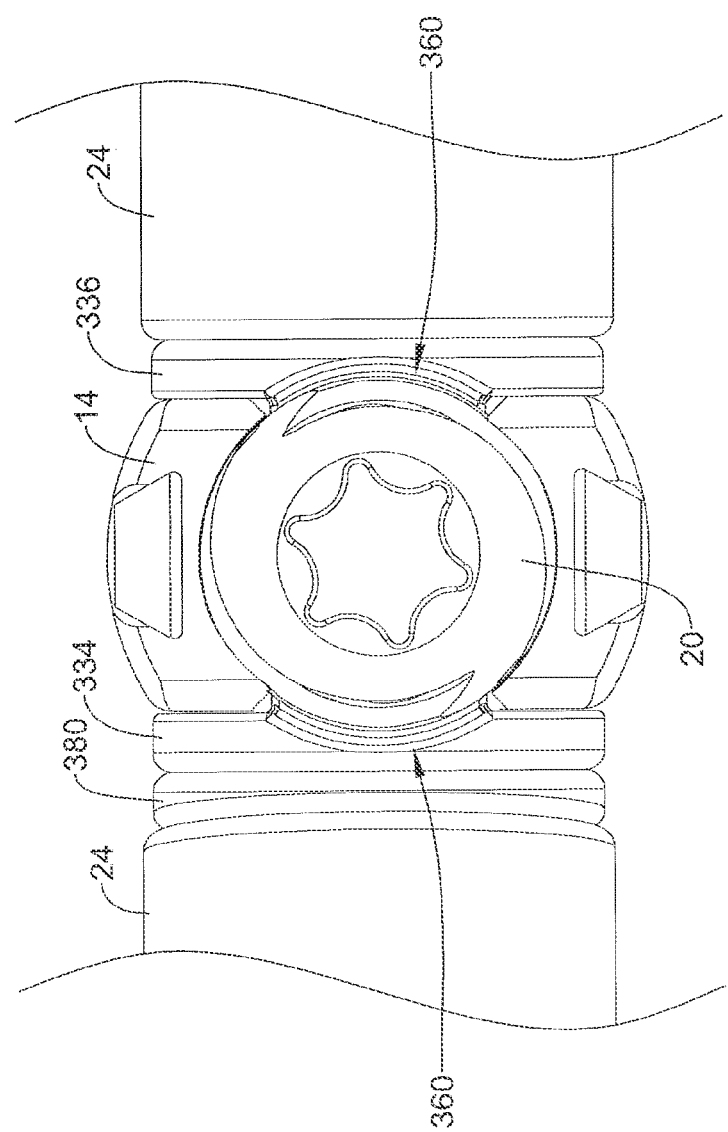
FIG. 19 is a top view of a portion of the spinal stabilization system of FIG. 17A.

The insert 332 can also include recesses 360 formed in the flanges 334, 336 of the insert 332 to accommodate the fastener 20 therebetween. For instance, as shown in FIG. 19, the fastener 20 can have an outer diameter greater than the distance between the first flange 334 and the second flange 336 (i.e., the distance between the inner surfaces of the flanges 334, 336 facing the medial portion 338. Thus, the recesses 360 can provide clearance for the fastener 20 to be rotatably engaged with the housing 14 of the pedicle screw 12 between the first and second flanges 334, 336.

Figure 18A:
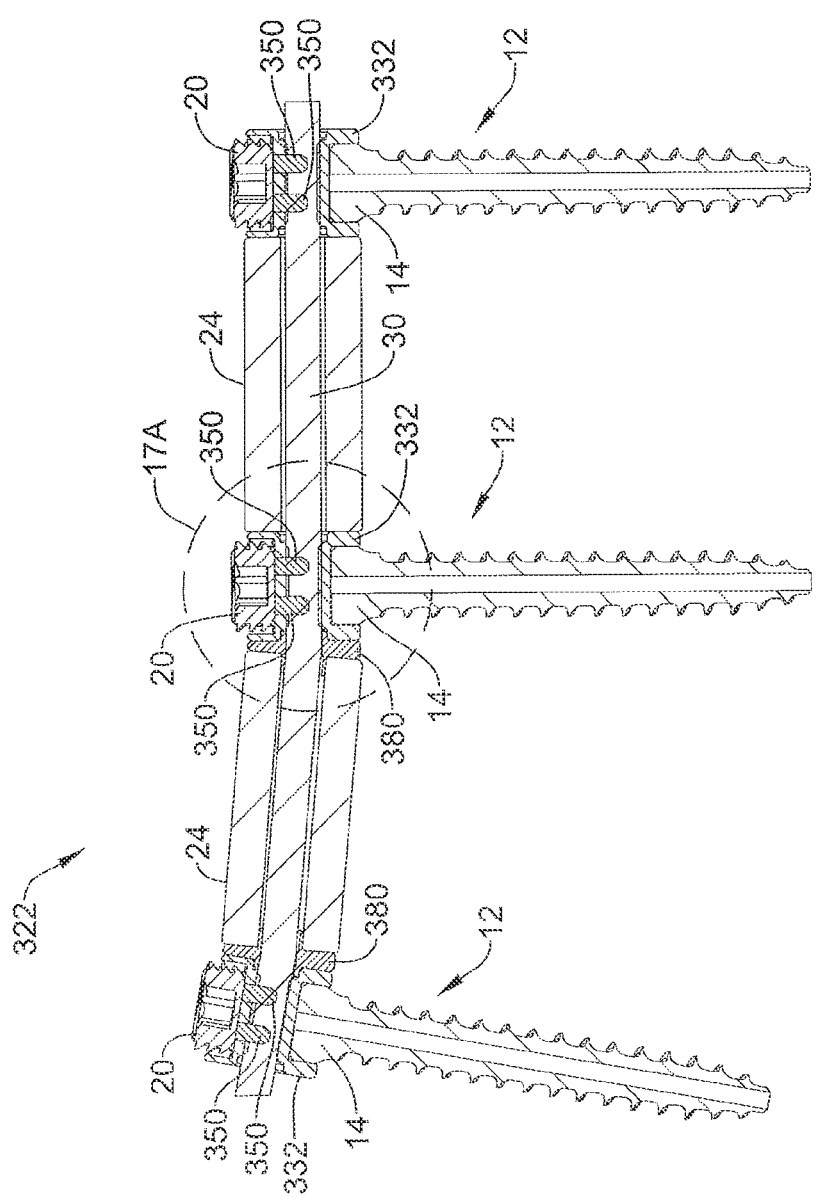
FIG. 18A is a longitudinal cross-sectional view of a spinal stabilization system utilizing the components of FIG. 16.

FIG. 18A illustrates a support construct 322 utilizing inserts 332. The support construct 322 can also include spacers 24 and a flexible member such as a flexible cord 30 extending through the spacers 24, as well as other components if desired. The inserts 332 are shown positioned in the housing 14 of the pedicle screws 12, with spacers 24 positioned between adjacent inserts 332. The flexible cord 30 can extend through the bores 340 of the inserts 332 and the lumen of the spacers 24. The fasteners 20 can be threadably engaged with the housing 14 of the pedicle screws 12 to secure the inserts 332 to the housing 14. In some instances, the fasteners 20 can drive the pins 350 into clamping engagement with the cord 30 as the fasteners 20 are threadably engaged with the housing 14 of the pedicle screw 12. In other instances, the drive pins 350 can be pressed against the cord 30 prior to inserting the inserts 332 into the housing 14 of the pedicle screw 12.

The support construct 322 can also include one or more rings 380 positionable between an end surface of an insert 332 and an end surface of a spacer 24. In some instances, the use of the ring 380 can between the insert 332 and the spacer 24 can provide a desired amount of angulation between the longitudinal axis of the bore 340 of the insert 332 relative to the lumen of the spacer 24 such that the central axis of the lumen of the spacer 24 extends non-parallel (e.g., oblique) to the central axis of the bore 340 of the insert 332.

Figure 18B:
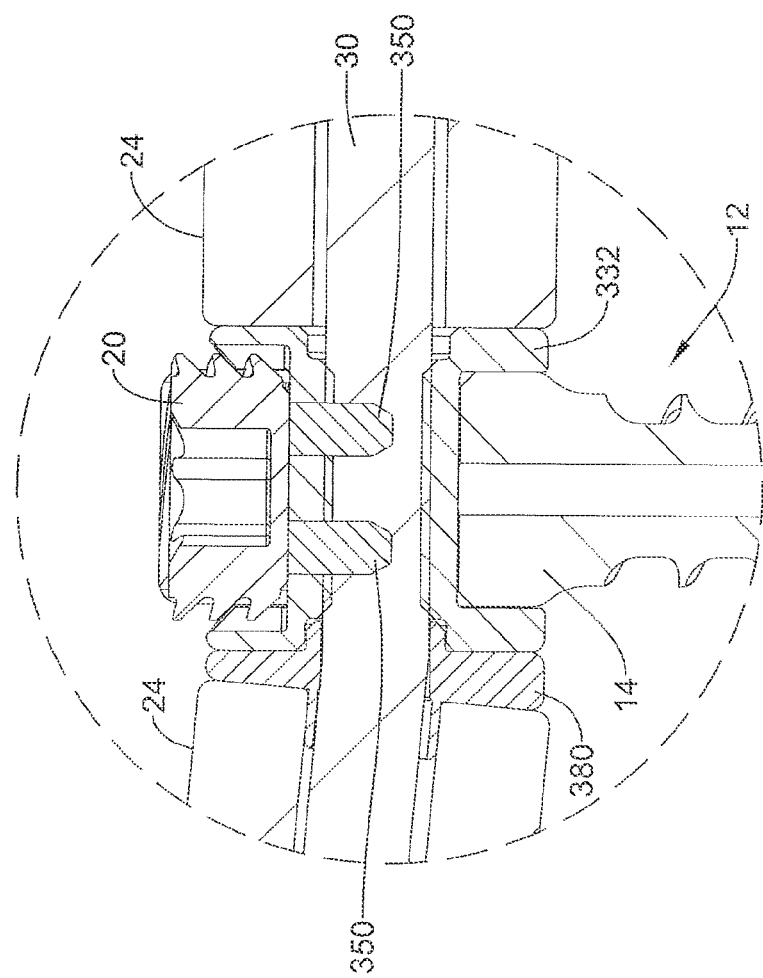
FIG. 18B is an enlarged view of a portion of FIG. 17A.

As shown in the enlarged view of FIG. 18B, the ring 380 can include an annular portion 382 with an opening 388 extending axially through the annular portion 382 for receiving the cord 30 therethrough. The annular portion 382 can have a first face 392 configured to face and abut an end surface of a flange of the insert 332 and an opposite, second face 394 configured to face and abut an end surface of a spacer 24. The first face 392 can be non-parallel to the second face 394 providing the annular portion 382 with a wedge-shape. The angle between the first face 392 and the second face 394 can be any desired angle, such as 2°, 3°, 4°, 5°, 6°, 7°, 8°, 9° or 10°, for example.

In some instances the ring 380 can include an annular projection 384 extending from the second face 394 of the annular portion 382. The opening 388 can extend through the annular projection 384, and thus the cord 30 can extend through the annular projection 384. The annular projection 384 can be configured to extend into the lumen of the spacer 24, such as an enlarged recessed portion at an end region of the spacer 24. Additionally or alternatively, the ring 380 can include annular projection 386 extending from the first face 392 of the annular portion 382. The opening 388 can extend through the annular projection 386, and thus the cord 30 can extend through the annular projection 386. The annular projection 386 can be configured to extend into the bore 340 of the insert 332, such as an enlarged recessed portion in a flange of the insert 332.

In some instances, the ring 380 can include an engagement feature configured to mate with an engagement feature of the insert 332 and/or the spacer 24 to orient the ring 380 at a desired rotational position relative to the insert 332 positioned on a first side of the ring 380 and/or the spacer 24 positioned on a second side of the ring 380.

Figure 20:
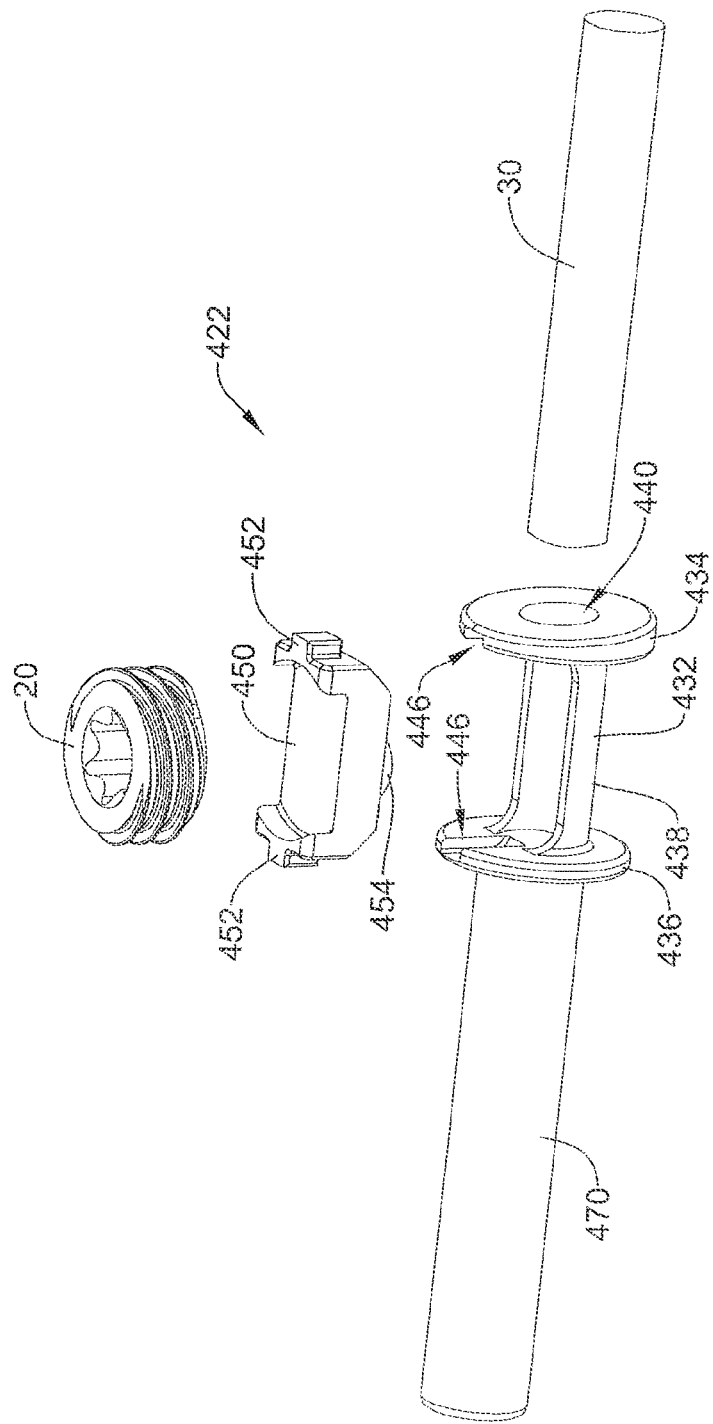
FIG. 20 is an exploded view of components of another spinal stabilization system.
Figure 21:
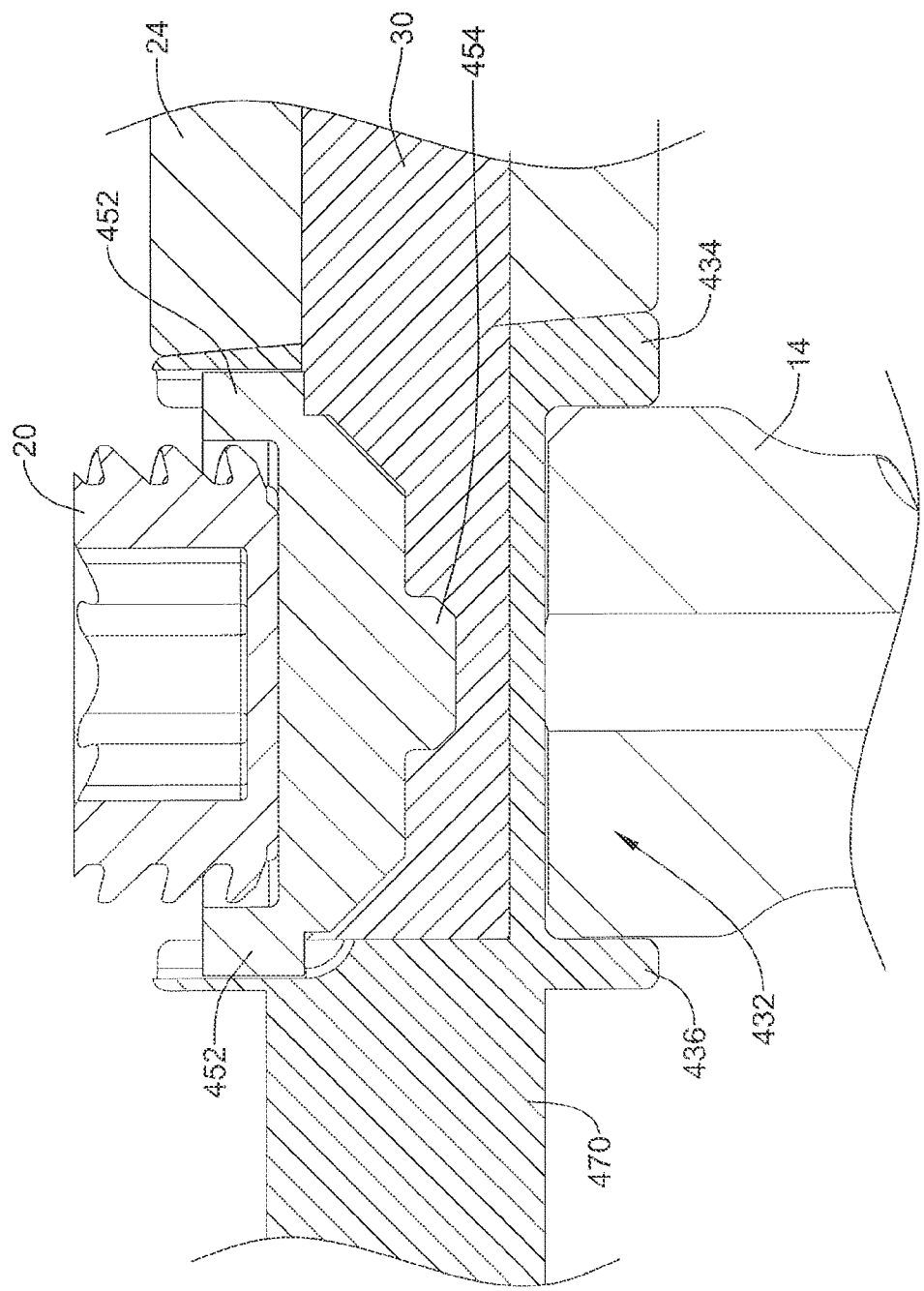
FIG. 21 is a longitudinal cross-sectional view of the spinal stabilization system of FIG. 19.

FIGS. 20 and 21 illustrate components of another support construct 422 including a rigid segment coupled to a flexible segment. The support construct 422 can include an insert 432 positionable in the housing 14 of a pedicle screw 12 or other vertebral anchor, forming a transition between a rigid segment and a flexible segment of the support construct 422. For example, the rigid segment can include a rigid rod member 470 and the flexible segment can include a spacer 24, and a flexible member such as a flexible cord 30 extending through the spacer 24, as well as other components if desired. The end of the cord 30 can be secured to the rigid rod member 470, via the insert 432, providing a transition between the dynamic or flexible portion of the construct 422 and the rigid portion of the construct 422.

The insert 432 can include a first flange 434 and a second flange 436 spaced from the first flange 434 by a medial region 438. The medial region 438 can have a cross-sectional dimension less than the cross-sectional dimension of each of the first and second flanges 434, 436. For instance, the medial region 438 can be sized for insertion into the U-shaped channel of the housing 14 of a pedicle screw 12 or other vertebral anchor, with the first flange 434 located exterior of the housing 14 on a first side of the housing 14 and the second flange 436 located exterior of the housing 14 on a second side of the housing 14, similar to other inserts described herein.

The rigid rod member 470 can extend from the second flange 436. In some instances the rigid rod member 470 can be integrally formed with the insert 432 as a monolithic construct, however, in other instances the rigid rod member 470 can be a separate component attached to the insert 432, for example. The rigid rod 470 can be sized to extend to one or more additional pedicle screws (not shown), for example. The rigid rod 470 can be any desired length, such as a length sufficient to extend between two, three, four, or more pedicle screws 12 secured to corresponding vertebrae of the spinal column.

The insert 432 can include a bore 440 extending into the medial region 438 from the first flange 434 for receiving a portion of the flexible cord 30, such as an end portion of the flexible cord 30. The insert 432 can also include a clamping member 450 configured to clamp or secure the cord 30 within the bore 440 of the insert 432. For example, the clamping member 450 can be movable relative to the medial portion 438 of the insert 432 to clamp the cord 30 between the clamping member 450 and the medial portion 438.

The clamping member 450 can be constructed similar to the clamping member 150, discussed above. For example, the clamping member 450 can include a first tab 452 extending into a channel 446 in the first flange 434 and a second tab 452 extending into a channel 446 in the second flange 436. The tabs 452 can move along the channels 446 as the clamping member 450 is moved toward the cord 30 to clamp the cord 30 in the bore 440. In some instances, the tabs 452 can form an interference fit with the channels 446 such that walls of the tabs 452 frictionally engage walls of the channels 446 to resist movement of the clamping member 450 relative to the medial portion 438 of the insert 432 unless and until the force sufficient to overcome the frictional/interference force is overcome.

The clamping member 450 can include any mechanical gripping means such as, but not limited to, one or more ribs, projecting grooves, teeth, posts, spikes, and/or serrations or combination thereof for engaging and/or penetrating into the cord 30, in the illustrated embodiment, the clamping member 450 can include one or more, or a plurality of protuberances 454 configured to engage and/or penetrate into the cord 30.

It is noted that the insert 432 can alternatively be constructed to use any other clamping member to secure the cord 30 in the bore 440, such as any of the other clamping members described herein. Furthermore, it is noted that any of the other inserts described herein can include a rigid rod portion extending from one end of the insert for forming a rigid construct between two or more vertebrae.

FIG. 21 is a cross-sectional view of the support construct 422 in an assembled configuration, with the medial portion 438 positioned in the U-shaped channel of the housing 14 of a pedicle screw 12 and the flanges 434, 436 positioned on either side of the housing 14. In the assembled configuration, an end portion of the flexible cord 30 is positioned in the bore 440 of the insert 432 and the clamping member 450 is pressed into engagement with the cord 30 with the fastener 20.

The fastener 20 can then be engaged with the housing 14, such as through rotational movement of the fastener 20 relative to the housing 14. In some instances, the fastener 20 can include a threaded portion which threadably engages a threaded portion of the housing 14, such as internally threaded portions of opposing legs of the housing 14 defining the channel 15. Rotational movement of the fastener 20 moves the fastener 20 into engagement with the clamping member 450.

Although not shown, the rigid rod member 470 can extend to one or more additional pedicle screws which can be secured to corresponding vertebrae of the spinal column. Furthermore, the cord 30 can extend in an opposite direction from the insert 432 to one or more additional pedicle screws which can be secured to vertebrae of the spinal column. Furthermore, a spacer 24, such as that shown in FIG. 20, can be positioned between the flange 434 and another insert 432 and/or pedicle screw with the flexible cord 30 extending through the spacer 24, to provide a flexible construct at one or more vertebral levels.

Figure 22:
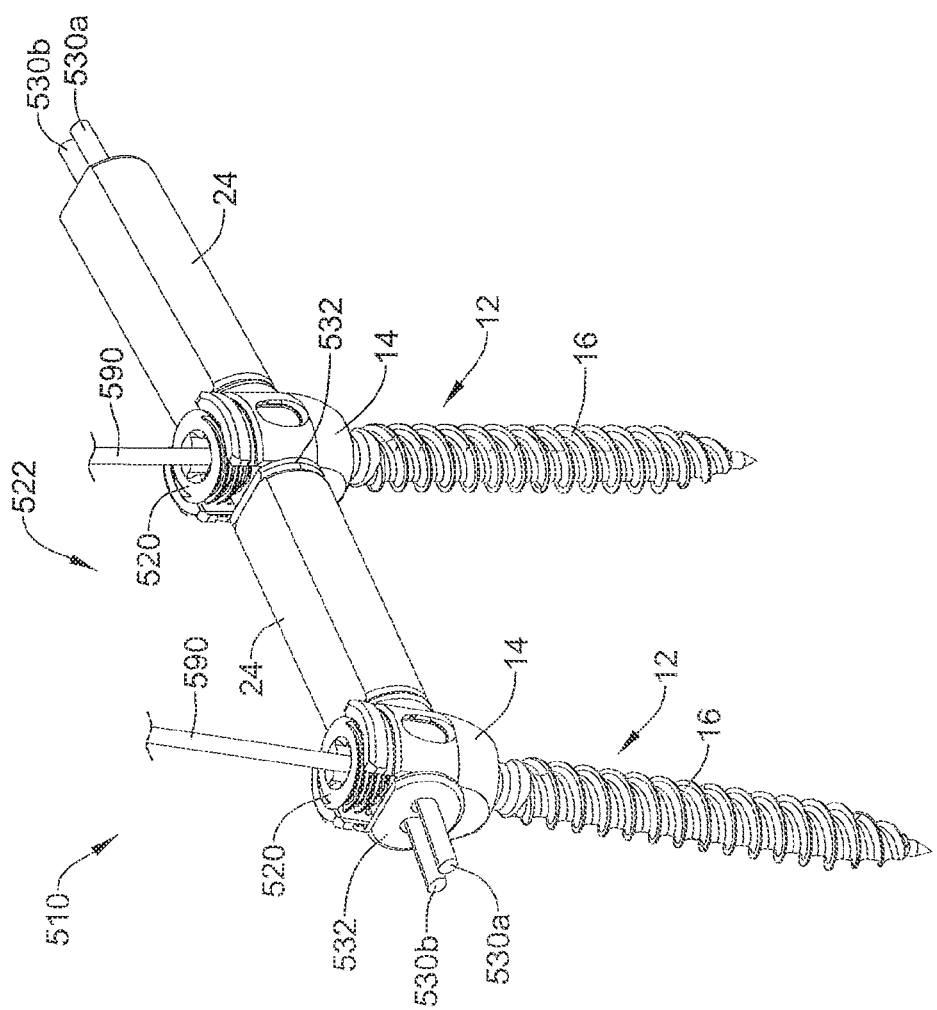
FIG. 22 is a perspective view of another spinal stabilization system.

Another spinal fixation system 510 for stabilizing a portion of a spinal column, such as one or more spinal segments of a spinal column is shown in FIG. 22. The spinal stabilization system 510 can include one or more or a plurality of vertebral anchors, depicted as pedicle screws 12, configured to be secured to a vertebra of a spinal column. The pedicle screws 12 can include a housing 14 and a shaft 16, which can include threads, extending from the housing 14. The pedicle screws 12 can be poly-axial, mono-axial or mono-planar, if desired. As shown in the cross-sectional view of FIG. 23A, the pedicle screws 12 can be cannulated (e.g., the threaded shaft 16 can having a central lumen extending longitudinally therethrough) to be delivered to the anatomy over a K-wire 590.

The pedicle screw 12 can include a securing element, such as a threaded fastener 520 (e.g., a set screw, cap) configured to rotatably engage the housing 14 to secure a portion of a support construct 522 to the pedicle screw 12. The fastener 520 can be rotatably engaged between spaced apart legs of the housing 14 which define a channel of the housing 14 therebetween. The fastener 520 can also be cannulated to be advanced to the housing 14 of the pedicle screw along a K-wire 590

The spinal stabilization system 510 can also include one or more, or a plurality of support constructs 522 extending between pedicle screws 12 of the spinal stabilization system 510. The support construct 522 can be constructed of a plurality of components in some instances. For instance, the support construct 522 can include spacers 24, and a plurality of flexible members such as a first flexible cord 530a and a second flexible cord 530b extending through the spacers 24, as well as other components if desired. The cords 530a, 530b can extend from the housing 14 of the first pedicle screw 12 to the housing 14 of the second pedicle screw 12.

Figure 23A:
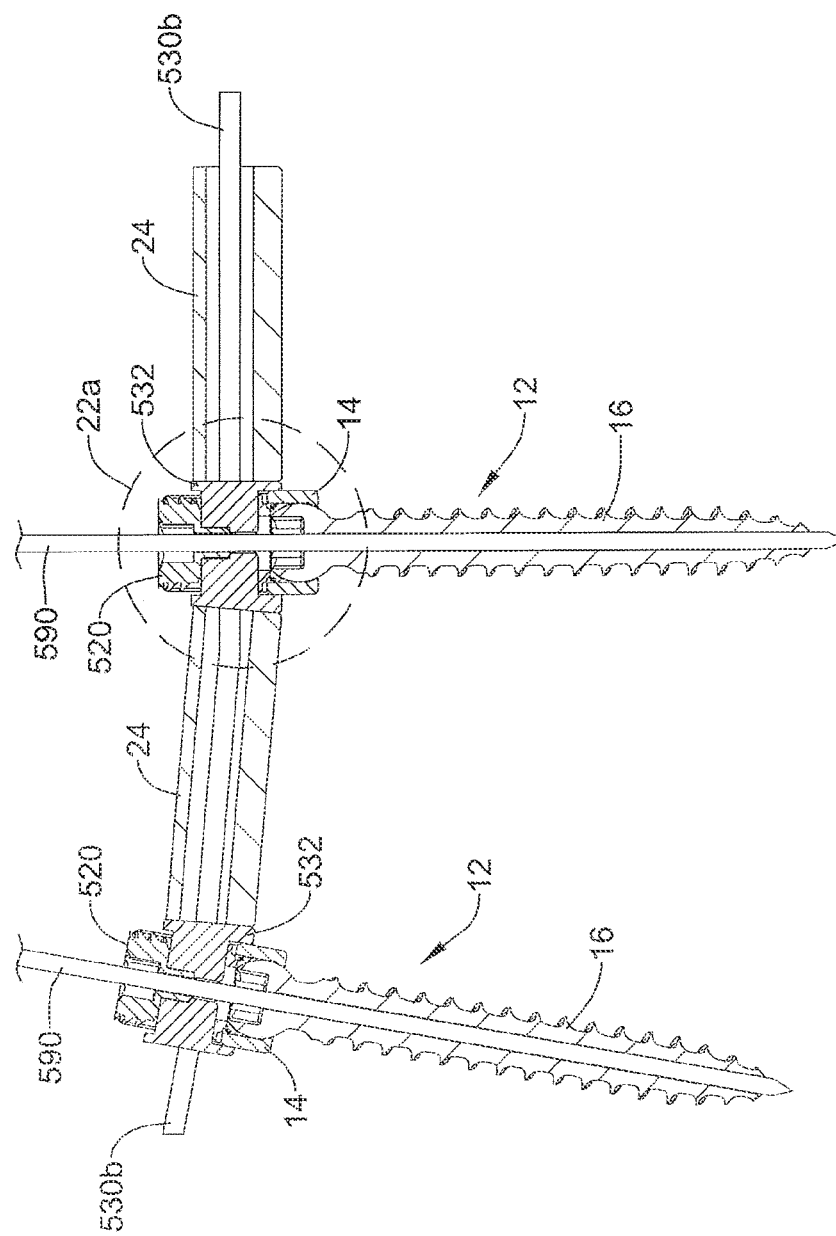
FIG. 23A is a longitudinal cross-sectional view of the spinal stabilization system of FIG. 22.

In some embodiments, the spacers 24 can have a lumen extending from a first end to a second end of the spacer 24, as shown in FIG. 23A, for receiving the first and second flexible cords 530a, 530b therethrough. In other instances, the spacers 24 can include a plurality of lumens extending therethrough, each configured to receive a separate one of the plurality of flexible cords, for example. For instance, the spacer can include a first lumen configured to receive the first flexible cord 530a and a second lumen configured to receive the second flexible cord 530b, maintaining the first and second flexible cords 530a, 530b isolated from one another through the spacer 24.

When implanted in a patient, the cords 530a, 530b of the spinal stabilization system 510 can limit the range of flexion of the spinal segment, whereas the spacers 24 can limit the range of extension of the spinal segment. For instance, the cords 530a, 530b can be placed in tension and the spacers 24 can be placed in compression between the pedicle screws 12.

Figure 24:
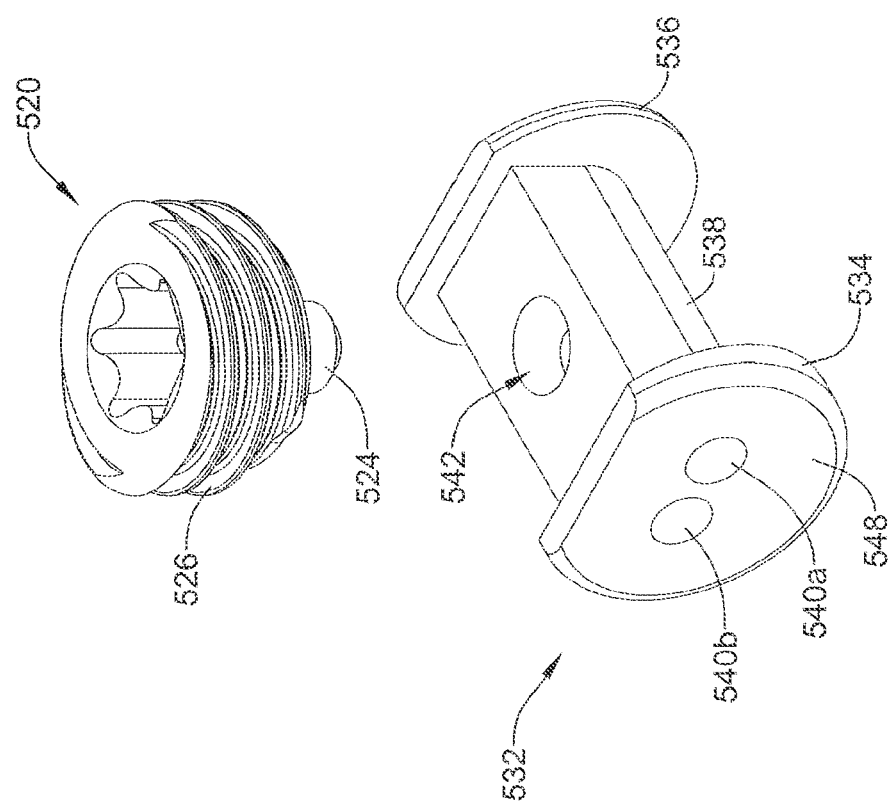
FIG. 24 is a perspective view of an insert and associated locking member of the spinal stabilization system of FIG. 22.

The spinal stabilization system 510 can also include inserts 532 configured to be inserted into the channels of the housings 14 of the pedicle screws 12. The insert 532 is further illustrated in FIGS. 24-26. The inserts 532, which can be considered spools in some instances, can include a first flange 534 proximate a first end of the insert 532, a second flange 536 proximate the second end of the insert 532, and a medial portion 538 intermediate the first flange 534 and the second flange 536 and extending therebetween. The insert 532 can have end surfaces 548 configured to abut an end surface of the spacers 24. For instance, when assembled an end surface 548 of an insert 532 coupled with the first pedicle screw 12 can abut an end surface of the spacer 24 proximate the first end of the spacer 24 and an end surface 548 of an insert 532 coupled with the second pedicle screw 12 can abut an end surface of the spacer 24 proximate the second end of the spacer 24.

The insert 532 can be configured such that the medial portion 538 is positionable in the channel of the housing 14 of the pedicle screw 12 with the first flange 534 positioned exterior of the housing 14 and facing the first side of the housing 14 and the second flange 536 positioned exterior of the housing 14 and facing the second side of the housing 14.

Figure 26:
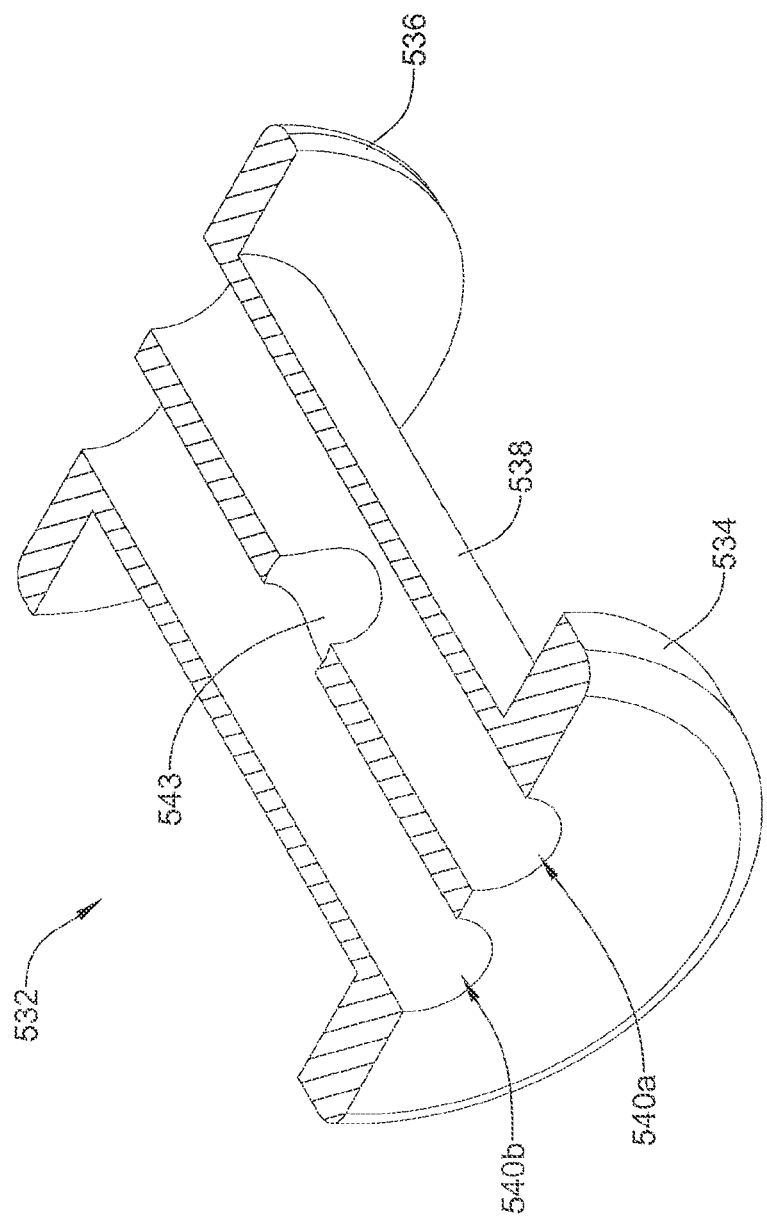
FIG. 26 is a cross-sectional view of the insert of FIG. 25.

The insert 532 can include a plurality of bores extending therethrough, such as a first bore 540a and a second bore 540b, each extending from a first end surface 548 at the first end of the insert 532 to a second end surface 548 at the second end of the insert 532. As shown in FIG. 26, the first bore 540a can extend generally parallel to and spaced apart from the second bore 540b, Each of the bores 540a, 54b can be configured to receive one of the cords 530a, 530b therein. For instance, the first cord 530a can be inserted into and/or through the first bore 540a of the insert 532 and the second cord 530b can be inserted into and/or through the second bore 540b of the insert 532.

Figure 25:
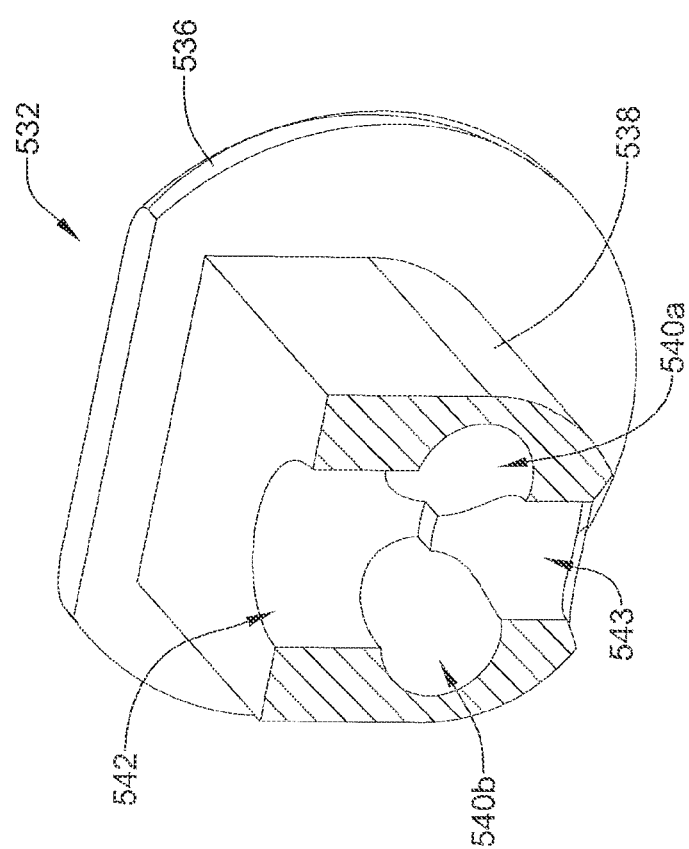
FIG. 25 is a cross-sectional view of the insert of FIG. 24.

The insert 532 can include an opening 542 in the medial portion 538 of the insert 532 for receiving a clamping member to bear against the cords 530a, 530b. As shown in FIG. 25, the opening 542 can intersect with each of the first and second bores 540a, 540b to provide direct engagement of the clamping member with a portion of each of the first and second cords 530a, 530b positioned in the bores 540a, 540b, respectively. In some instances, the insert 532 can include a lower portion 543 of the opening 542 extending below the first and second bores 540a, 540b such that the opening 542 extends entirely through the insert 532 from an upper surface to a lower surface of the medial portion 538 to accommodate the K-wire 590 extending through the opening 542 of the insert 532, as shown in FIG. 23A. In some instances, the insert 532 can be positioned in the channel of the housing 14 of the pedicle screw 12 with the first and second cords 530a, 530b extending through the first and second bores 540a, 540b of the insert 532 by advancing the insert 532 along the K-wire 590 (i.e., with the K-wire 590 extending through the opening 542) while the K-wire 590 is positioned through the longitudinal lumen extending through the shaft 16 of the pedicle screw 12 and the opening 542 through the insert 532. The K-wire 590 can extend through the opening 542 of the insert 532 with the K-wire 590 positioned between the first and second cords 530a, 530b. Thus, the longitudinal lumen extending through the shaft 16 of the pedicle screw 12 and the opening 542 through the insert 532 can be coaxially aligned, in some instances.

Figure 23B:
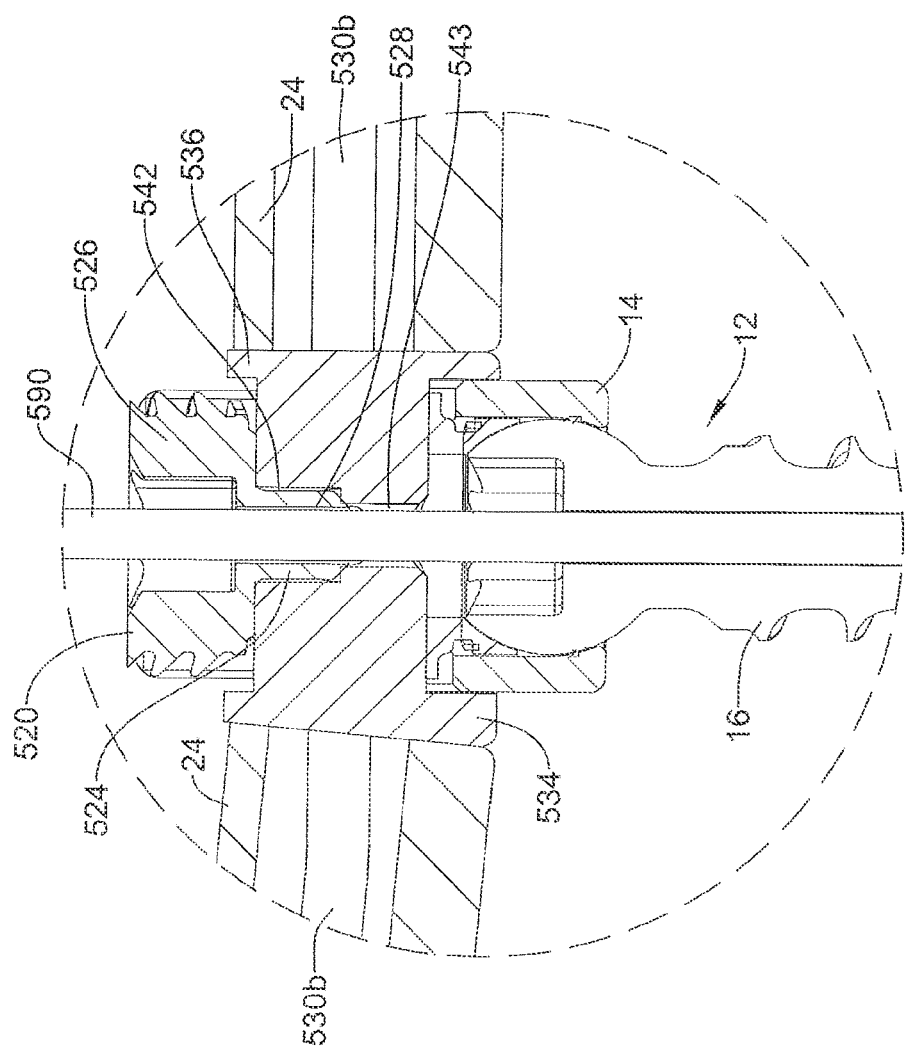
FIG. 23B is an enlarged view of a portion of FIG. 23A.
Figure 27:
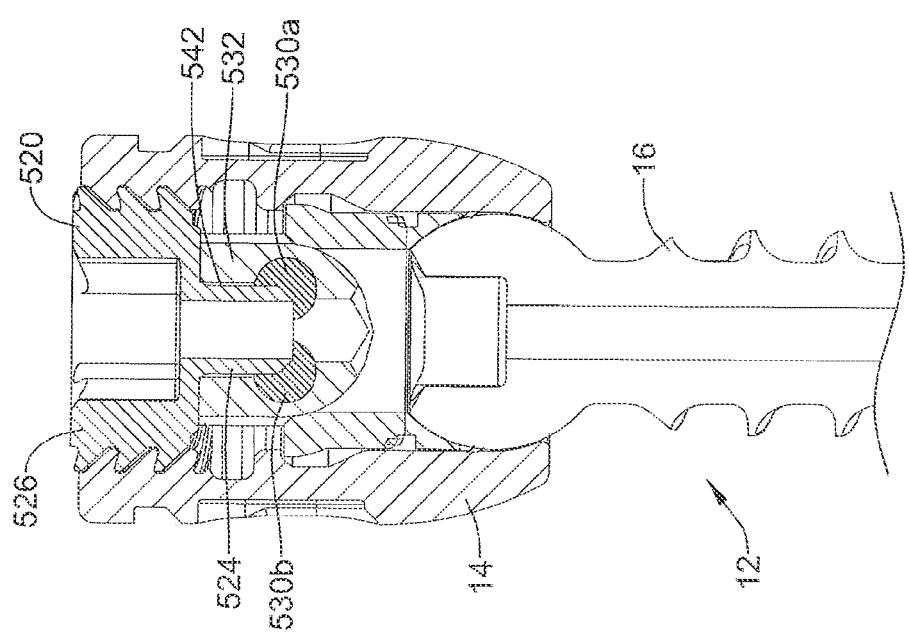
FIG. 27 is a cross-sectional view of the insert of FIG. 24 secured in the housing of a pedicle screw of the spinal stabilization system of FIG. 23A.

The clamping member can be a fastener 520, such as a threaded set screw including threads which mate with threads formed in the housing 14. The fastener 520 can be rotatably engaged between spaced apart legs of the housing 14 to apply a clamping force to the first and second cords 530a, 530b to clamp or secure the cords 530a, 530b within the first and second bores 540a, 540b of the insert 532 while simultaneously clamping the insert 532 in the housing 14 of a pedicle screw 12. For example, as shown in FIGS. 23B and 27, the fastener 520 can include a threaded portion 226 and a protuberance 224 extending from the threaded portion 226. As shown in FIG. 27, the protuberance 224 can extend into the opening 542 to bear against each of the first and second cords 530a, 530b and simultaneously clamp the first and second cords 530a, 530b in the first and second bores 540a, 540b, respectively. In some instances, the cords 530a, 530b can be clamped in the insert 532 with the fastener 520 while the K-wire 590 is positioned through the longitudinal lumen extending through the shaft 16 of the pedicle screw 12, the opening 542 through the insert 532, and the opening 528 through the fastener 520. Thus, the longitudinal lumen extending through the shaft 16 of the pedicle screw 12, the opening 542 through the insert 532, and the opening 528 through the fastener 520 can be coaxially aligned, in some instances.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

The invention claimed is:

1. A spinal system comprising:
   a threaded fastener;
   a housing of a vertebral anchor, the housing comprising two upwardly extending arms, each upwardly extending arm comprising an inner threaded surface to engage the threaded fastener;
   an insert positionable to extend through a channel formed by the two upwardly extending arms, the insert comprising:
   a first bore extending through the insert parallel to an insert longitudinal axis;
   a first flange positionable on a first exterior side of the housing of the vertebral anchor, a first interior surface of the first flange including a first channel extending outward from the first bore transverse to the insert longitudinal axis, wherein opposing sidewalls of the first channel are transverse to adjacent portions of the first interior surface along a length of the first channel;
   a second flange positionable on a second exterior side of the housing of the vertebral anchor, a second interior surface of the second flange including a second channel extending outward from the first bore transverse to the insert longitudinal axis, the first interior surface being in an opposing relationship with the second interior surface, wherein opposing sidewalls of the second channel are transverse to adjacent portions of the second interior surface along a length of the second channel and to first and second exterior surfaces opposing the first and second interior surfaces, respectively;
   a medial portion extending between the first flange and the second flange along the insert longitudinal axis that is transverse to an anchor longitudinal axis when positioned within the channel of the housing, the medial portion including an open superior portion, wherein the opposing sidewalls of each of the first and second channels extend towards a corresponding one of the first and second exterior surfaces of the first and second flanges, respectively; and
   a clamping member positionable within the open superior portion of the medial portion, the clamping member including a first tab and a second tab, the first tab configured to engage the first channel by being received within the first channel and the second tab configured to engage the second channel by being received within the second channel, the clamping member including a body portion extending between the first tab and the second tab comprising a lower surface and configured to engage a cord extending through the first bore and an upper surface configured to engage the threaded fastener, wherein the first and second channels retain and guide movement of the first and second tab, respectively, along the length of the first and second channels, respectively, in a radial direction transverse to the insert longitudinal axis and restrict movement of the first and second tab, respectively, in a lateral direction transverse to the radial direction, wherein the first and second channels each intersect the first bore, where each of the first and second channels extends from the first bore to an outer edge of the first flange and second flange, respectively, wherein the medial portion includes a rounded inferior portion configured to conform to the channel of the housing of the vertebral anchor, and wherein advancement of the threaded fastener relative to the inner threaded surfaces of the two upwardly extending arms to engage the upper surface of the clamping member simultaneously immobilizes the clamping member relative to the housing and the cord relative to the clamping member.

2. The spinal system of claim 1, wherein a plane of a first exterior surface of the first flange is transverse to an opposing plane of the first interior surface and a plane of a second exterior surface of the second flange is transverse to an opposing plane of the second interior surface and wherein the clamping member includes a flat superior surface extending between the first flange and the second flange.

3. The spinal system of claim 1, wherein each of the first and second channels terminates interiorly of an outer edge of the first flange and second flange, respectively, and wherein the clamping member includes a concave inferior surface configured to engage the cord.

4. The spinal system of claim 3, wherein a width of each of the first and second channels varies along a length of the first and second channels, respectively and wherein the concave inferior surface includes a plurality of raised gripping features adapted to engage the cord when the cord is extending through the first bore.

5. The spinal system of claim 4, wherein a width of an outer portion of each of the first and second channels is less than a width of an inner portion of each of the first and second channels, respectively and wherein the plurality of raised gripping features include a plurality of ribs aligned with the insert longitudinal axis upon insertion into an opening of the first bore.

6. The spinal system of claim 4, wherein the plurality of raised gripping features are selected from a group of raised gripping features including:
   ribs;
   projecting grooves;
   teeth;
   posts;
   spikes; and
   serrations.

7. The spinal system of claim 4, wherein each of the first and second tabs comprises more than one tab and each of the first and second channels comprise more than one channel to receive the first and second tabs, respectively, and wherein the plurality of raised gripping features are lands of a screw thread cut into the concave inferior surface.

8. The spinal system of claim 1, wherein the first and second channels each extends from an outer edge of the first flange and second flange, respectively, inwardly towards the first bore and terminates interiorly of the first bore, wherein an edge formed at an intersection of the first tab and a first end of an intermediate portion of the clamping member is generally parallel to the first channel, wherein an edge formed at an intersection of the second tab and an opposing second end of the intermediate portion of the clamping member is generally parallel to the second channel, and wherein the first tab and the second tab of the clamping member move along the anchor longitudinal axis to engage the cord.

9. The spinal system of claim 1, wherein each of the first and second channels intersects the first interior surface and opposing second exterior surface of a corresponding one of the first and second flanges, wherein the first bore comprises plural bores to receive plural cords, and wherein the clamping member includes a superior surface of the body portion configured to enable a set screw threaded into the housing of the vertebral anchor to engage the superior surface and drive the clamping member into the cord.

10. An insert adapted to be received within a saddle portion of a vertebral anchor, the insert comprising:
   a first flange configured to engage a first exterior side of the saddle portion of the vertebral anchor;
   a second flange configured to engage a second exterior side of the saddle portion of the vertebral anchor;
   a medial portion extending between the first flange and the second flange along an insert longitudinal axis that is transverse to an anchor longitudinal axis of the vertebral anchor when positioned within the saddle portion, the medial portion including a U-shaped body conforming to the saddle portion of the vertebral anchor;
   a first bore extending through the first flange, the medial portion, and the second flange parallel to the insert longitudinal axis, and adapted to receive a cord extending through the insert; and
   a clamping member including opposing tabs configured to engage a first channel in a first interior sidewall of the first flange and a second channel in an opposing second interior sidewall of the second flange, the clamping member configured to engage the cord through an opening in the U-shaped body of the medial portion, wherein a base of each of the first and second channels is spatially offset from an adjacent portion of a corresponding one of the first and second opposing interior sidewalls of the first and second flanges and extends outwardly from the first bore transverse to the insert longitudinal axis, wherein the first and second channels retain and guide movement of the first and second tabs, respectively, along a length of the first and second channels, respectively, in a radial direction transverse to the insert longitudinal axis and restrict movement of the first and second tabs, respectively, in a lateral direction transverse to the radial direction; wherein the first and second channels each intersects and extends from the first bore to an outer edge of the first flange and second flange, respectively, and wherein the first channel and the second channel each extends radially outward from the first bore along the first and second opposing interior sidewalls of the first flange and the second flange, respectively.

11. The insert of claim 10, wherein a plane of a first exterior sidewall of the first flange is transverse to an opposing plane of the first interior sidewall and a plane of a second exterior sidewall of the second flange is transverse to an opposing plane of the second interior sidewall and wherein the first interior sidewall engages the first exterior side of the saddle portion.

12. The insert of claim 11, wherein the first channel is indented in a portion of the first interior sidewall and wherein the first channel terminates interiorly of an outer edge of the first flange.

13. The insert of claim 11, wherein the first and second channels each extends from an outer edge of the first flange and second flange, respectively, inwardly towards the first bore and terminates interiorly of the first bore, and wherein the first exterior sidewall forms an oblique angle with respect to the insert longitudinal axis, and the first interior sidewall is perpendicular to the insert longitudinal axis.

14. The insert of claim 10, wherein a width of each of the first and second channels varies along a length of the first and second channels, respectively and wherein an inferior surface of the clamping member forms a concave engagement surface.

15. The insert of claim 14, wherein a width of an outer portion of each of the first and second channels is less than a width of an inner portion of each of the first and second channels, respectively and wherein the concave engagement surface includes a plurality of raised gripping features adapted to engage the cord when extended through the first bore.

16. The insert of claim 15, wherein an edge formed at an intersection of the first tab and a first end of an intermediate portion of the clamping member is generally parallel to the first channel, wherein an edge formed at an intersection of the second tab and an opposing second end of the intermediate portion of the clamping member is generally parallel to the second channel, and wherein the plurality of raised gripping features include a plurality of ribs aligned with the insert longitudinal axis upon insertion into the opening.

17. The insert of claim 15, wherein the plurality of raised gripping features are selected from a group of gripping features including:
   ribs;
   projecting grooves;
   teeth;
   posts;
   spikes; and
   serrations.

18. The insert of claim 15, wherein each of the first and second tabs comprises more than one tab and each of the first and second channels comprise more than one channel to receive the first and second tabs, respectively, and wherein the plurality of raised gripping features are formed by a screw thread cut into the concave engagement surface.

19. The insert of claim 15, wherein the first bore comprises plural bores to receive plural cords and wherein the first bore includes a second plurality of raised gripping features along a length opposite the clamping member.

20. A spinal system comprising:
   an insert positionable to extend through a channel formed by two upward extending arms of a housing of a vertebral anchor, the insert comprising:
   a first bore extending through the insert parallel to an insert longitudinal axis;
   a first flange positionable on a first exterior side of the housing of the vertebral anchor, a first interior surface of the first flange including a first channel intersecting and extending outward from the first bore transverse to the insert longitudinal axis;
   a second flange positionable on a second exterior side of the housing of the vertebral anchor, a second interior surface of the second flange including a second channel intersecting and extending outward from the first bore transverse to the insert longitudinal axis, the first interior surface being in an opposing relationship with the second interior surface;
   a medial portion extending between the first flange and the second flange along the insert longitudinal axis that is transverse to an anchor longitudinal axis when positioned within the channel of the housing, the medial portion including an open superior portion; and
   a clamping member including a first tab and a second tab, the first tab configured to engage the first channel and the second tab configured to engage the second channel, the clamping member including a body portion extending between the first tab and the second tab and configured to engage a cord extending through the first bore, wherein the first and second channels retain and guide movement of the first and second tab, respectively, transverse to the insert longitudinal axis, wherein a width of an outer portion of each of the first and second channels is less than a width of an inner portion of each of the first and second channels, respectively.

* * * * *